(12) United States Patent
Walsh et al.

(10) Patent No.: US 12,037,311 B2
(45) Date of Patent: Jul. 16, 2024

(54) PRE-ASSEMBLED, PROTECTED, CHEMICALLY STABLE, CHEMOSELECTIVE LINKERS

(71) Applicant: Cowper Sciences Inc., Chandler, AZ (US)

(72) Inventors: Patrick Walsh, Chandler, AZ (US); David Smith, Scottsdale, AZ (US); Gaurav Saini, Chandler, AZ (US); Jae H. Park, Gainsville, FL (US)

(73) Assignee: COWPER SCIENCES INC., Chandler, AZ (US)

( * ) Notice: Subject to any disclaimer, the term of this patent is extended or adjusted under 35 U.S.C. 154(b) by 997 days.

(21) Appl. No.: 16/348,484

(22) PCT Filed: Nov. 8, 2017

(86) PCT No.: PCT/US2017/060721
§ 371 (c)(1),
(2) Date: May 8, 2019

(87) PCT Pub. No.: WO2018/089554
PCT Pub. Date: May 17, 2018

(65) Prior Publication Data
US 2019/0359566 A1    Nov. 28, 2019

Related U.S. Application Data

(60) Provisional application No. 62/419,861, filed on Nov. 9, 2016.

(51) Int. Cl.
| | | |
|---|---|---|
| C07C 323/67 | (2006.01) | |
| A61P 1/04 | (2006.01) | |
| A61P 19/02 | (2006.01) | |
| A61P 29/00 | (2006.01) | |
| A61P 31/00 | (2006.01) | |
| A61P 31/04 | (2006.01) | |
| A61P 31/10 | (2006.01) | |
| A61P 31/12 | (2006.01) | |
| A61P 33/00 | (2006.01) | |
| A61P 35/00 | (2006.01) | |
| A61P 37/02 | (2006.01) | |
| C07C 311/51 | (2006.01) | |
| C07C 311/52 | (2006.01) | |
| C07F 7/18 | (2006.01) | |
| G01N 33/543 | (2006.01) | |

(Continued)

(52) U.S. Cl.
CPC .......... *C07C 323/67* (2013.01); *C07C 311/52* (2013.01); *C07F 7/1804* (2013.01); *G01N 33/54306* (2013.01); *G01N 33/54393* (2013.01); *G01N 33/564* (2013.01); *G01N 33/574* (2013.01); *G01N 33/56911* (2013.01); *G01N 33/56961* (2013.01); *G01N 33/56983* (2013.01); *G01N 33/68* (2013.01); *G01N 2800/065* (2013.01); *G01N 2800/102* (2013.01); *G01N 2800/104* (2013.01)

(58) Field of Classification Search
CPC ... C07C 323/67; C07C 311/52; C07C 311/51; C07C 2603/18; C07F 7/1804; C07F 7/0838; C07F 7/087; A61P 1/04; A61P 19/02; A61P 20/00; A61P 31/00; A61P 31/04; A61P 31/10; A61P 31/12; A61P 33/00; A61P 35/00; A61P 37/02; G01N 33/54306; G01N 33/54393; G01N 33/564; G01N 33/574; G01N 33/56911; G01N 33/56961; G01N 33/56983; G01N 33/68; G01N 2800/065; G01N 2800/102; G01N 2800/104; G01N 2800/52
See application file for complete search history.

(56) References Cited

U.S. PATENT DOCUMENTS

| 5,143,854 A | 9/1992 | Pirrung et al. |
|---|---|---|
| 5,424,186 A | 6/1995 | Fodor et al. |

(Continued)

FOREIGN PATENT DOCUMENTS

| CN | 1282105 A | 1/2001 |
|---|---|---|
| CN | 102753620 A | 10/2012 |

(Continued)

OTHER PUBLICATIONS

De Paz, J.L. et la. Exploration of the use of an acylsulfonamide safety-catch linker for the polymer-supported synthesis of hyaluronic acid oligosaccharides. Carbohydr Res. Mar. 30, 2010;345(5):565-71. Epub Jan. 4, 2010.
Mitra et al., Self-assembly of cyclic metal-DNA nanostructures using ruthenium tris(bipyridine)-branchedoligonucleotides. Agnewandte Chemie. 43(43):5804-5808 (2004).
No Author Pubchem CID 110154. Created: Aug. 8, 2005. Date accessed: Feb. 26, 2018, pp. 1-15.
PCT/US2017/060721 International Search Report and Written Opinion dated Feb. 26, 2018.

(Continued)

*Primary Examiner* — Sun Jae Yoo
(74) *Attorney, Agent, or Firm* — WILSON SONSINI GOODRICH & ROSATI

(57) ABSTRACT

Molecules compounds are provided having the structure in Formula I, or a salt thereof, wherein n1 is independently 0, 1, 2, or 3; n2 is 0, 1, 2, 3, 4, 5, 6, 7, 8, 9, 10, 11, 12, 13, 14, 15, 16, 17, 18, 19, or 20; n3 is from 0, 1, 2, or 3; n4 is 0 or 1; and n5 is 0, 1, 2, or 3; and wherein X is O, N, or S; Y, Z, XX, and YY are the same or different and are independently O or S; ZZ comprises nitrogen, oxygen, sulfur, or selenium; and wherein $R^1$, $R^2$, $R^3$, $R^4$, $R^5$, $R^6$, $R^7$, $R^8$, $R^9$, $R^{10}$, $R^{11}$, $R^{12}$ are as described herein. Methods are also provided for the synthesis of and use of the provided molecules in applications for diagnostic testing.

23 Claims, 37 Drawing Sheets

(51) Int. Cl.
  *G01N 33/564* (2006.01)
  *G01N 33/574* (2006.01)
  *G01N 33/68* (2006.01)
  *G01N 33/569* (2006.01)

(56) References Cited

U.S. PATENT DOCUMENTS

| | | | |
|---|---|---|---|
| 5,571,639 | A | 11/1996 | Hubbell et al. |
| 5,932,546 | A | 8/1999 | Barrett et al. |
| 5,981,478 | A | 11/1999 | Ruoslahti et al. |
| 7,270,950 | B2 | 9/2007 | Szostak et al. |
| 7,507,480 | B2 | 3/2009 | Sugama |
| 7,884,183 | B2 | 2/2011 | Von Wronski et al. |
| 7,884,783 | B2 | 2/2011 | Choi |
| 7,909,889 | B2 | 3/2011 | Charrier et al. |
| 9,482,666 | B2 | 11/2016 | Domenyuk et al. |
| 9,970,932 | B2 | 5/2018 | Woodbury et al. |
| 2003/0003223 | A1 | 1/2003 | Morse et al. |
| 2003/0044833 | A1 | 3/2003 | Benchikh et al. |
| 2003/0219816 | A1 | 11/2003 | Solomon et al. |
| 2004/0092396 | A1 | 5/2004 | Glazer et al. |
| 2004/0126890 | A1 | 7/2004 | Gjerde et al. |
| 2005/0255491 | A1 | 11/2005 | Lee et al. |
| 2006/0013971 | A1 | 1/2006 | Chen et al. |
| 2006/0074251 | A1 | 4/2006 | Jung |
| 2006/0210452 | A1 | 9/2006 | Fodor et al. |
| 2007/0248985 | A1 | 10/2007 | Dutta et al. |
| 2008/0020507 | A1 | 1/2008 | Nomura |
| 2008/0146459 | A1 | 6/2008 | Iwakura et al. |
| 2008/0207507 | A1 | 8/2008 | Lau et al. |
| 2008/0214405 | A1 | 9/2008 | Chen et al. |
| 2009/0054251 | A1 | 2/2009 | O'Connor et al. |
| 2009/0142792 | A1 | 6/2009 | Robinson et al. |
| 2009/0176664 | A1 | 7/2009 | Chu |
| 2009/0285798 | A1 | 11/2009 | Vita et al. |
| 2011/0014222 | A1 | 1/2011 | Gonzalez |
| 2011/0319291 | A1 | 12/2011 | Vrijbloed et al. |
| 2012/0004130 | A1 | 1/2012 | Mattoon et al. |
| 2012/0190574 | A1 | 7/2012 | Johnston et al. |
| 2012/0228155 | A1 | 9/2012 | Clare et al. |
| 2012/0237555 | A1 | 9/2012 | Williams et al. |
| 2012/0238477 | A1 | 9/2012 | Albert et al. |
| 2013/0071860 | A1 | 3/2013 | Hale et al. |
| 2013/0079250 | A1 | 3/2013 | Johnston et al. |
| 2013/0095548 | A1 | 4/2013 | Jain et al. |
| 2013/0310265 | A1 | 11/2013 | Menegatti et al. |
| 2014/0087963 | A1 | 3/2014 | Johnston et al. |
| 2015/0217258 | A1 | 8/2015 | Woodbury et al. |
| 2015/0241420 | A1 | 8/2015 | Johnston et al. |
| 2016/0041158 | A1 | 2/2016 | Woodbury et al. |
| 2016/0052990 | A1 | 2/2016 | Ring et al. |
| 2016/0060687 | A1 | 3/2016 | Zhu et al. |
| 2016/0067667 | A1 | 3/2016 | Rajasekaran et al. |
| 2016/0090592 | A1 | 3/2016 | Banyai et al. |
| 2016/0367961 | A1 | 12/2016 | Patel et al. |
| 2017/0030906 | A1 | 2/2017 | Mesa et al. |
| 2019/0113522 | A1 | 4/2019 | Greving et al. |
| 2019/0359854 | A1 | 11/2019 | Saini et al. |
| 2020/0116715 | A1 | 4/2020 | Gerwien et al. |
| 2020/0407712 | A1 | 12/2020 | Boyd et al. |

FOREIGN PATENT DOCUMENTS

| | | |
|---|---|---|
| WO | WO-02081649 A2 | 10/2002 |
| WO | WO-2004053068 A2 | 6/2004 |
| WO | WO-2011041586 A1 | 4/2011 |
| WO | WO-2014006124 A1 | 1/2014 |
| WO | WO-2014039718 A1 | 3/2014 |
| WO | WO-2014062981 A1 | 4/2014 |
| WO | WO-2017173365 A1 | 10/2017 |
| WO | WO-2018089554 A1 | 5/2018 |
| WO | WO-2018089556 A1 | 5/2018 |
| WO | WO-2018236838 A2 | 12/2018 |
| WO | WO-2019157362 A1 | 8/2019 |
| WO | WO-2020102365 A1 | 5/2020 |

OTHER PUBLICATIONS

PCT/US2017/060724 International Search Report and Written Opinion dated Mar. 13, 2018.
PCT/US2018/038240 International Search Report and Written Opinion dated Dec. 27, 2018.
PCT/US2019/017326 International Search Report and Written Opinion dated Jun. 3, 2019.
PCT/US2019/017326 Invitation to Pay Additional Fees dated Apr. 12, 2019.
Gardner et al.: Functional screening for anti-CMV biologics identifies a broadly neutralizing epitope of an essential envelope protein. Nat Commun. 7:13627 doi:10.1038/ncomms13627 [1-15](2016).
Huang et al., Hydrogen/Deuterium Exchange Mass Spectrometry and Computational Modeling Reveal a Discontinuous Epitope of an Antibofy/TL1A Interaction MABS 101(1): 95-103 (2017).
Hundsberger et al.: Assembly and use of high-density recombinant peptide chips for large-scale ligand screening is a practical alternative to synthetic peptide libraries. BMC Genomics 18(1):450 doi:10.1186/s12864-017-3814-3 [1-10](2017).
Marthandan et al.: Construction and evaluation of an automated light directed protein-detecting microarray synthesizer. IEEE Trans Nanobioscience 7(1):20-27 doi:10.1109/TNB.2008.2000146 (2008).
PCT/US19/61196 International Search Report and Written Opinion dated Feb. 27, 2020.
Timmerman et al.: A combinatorial approach for the design of complementarity-determining region-derived peptidomimetics with in vitro anti-tumoral activity. J Biol Chem. 284(49):34126-34134 doi:10.1074/jbc.M109.041459 (2009).
U.S. Appl. No. 16/968,512 Final Office Action dated Jan. 21, 2022.
Sales et al.: Epoxide silylant agent ethylenediamine reaction product anchored on silica gel—thermodynamics of cation-nitrogen interaction at solid/liquid interface. Journal of Non-Crystalline Solids 330(1-3):142-149 (2003).
Calvo et al. The mitochondrial proteome and human disease. Annu. Rev. Genomics Hum Genet 11:25-44 (2010).
Cao et al., Dextran-silane coating chemistry for $SiO_2$-based suspension array system. Polym Chem 2: 2574-2580 (2011).
Crooks, et al. WebLogo: a sequence logo generator. Genome Res. Jun. 2004;14(6):1188-90.
England et al., A potent dimeric peptide antagonist of interleukin-5 that binds two interleukin-5 receptor α chains. PNAS 97 (12): 6862-6867 (2000).
Gizdavic-Nikolaidis et al., Spectroscopic characterization of GPTM/DETA and GPTMS/EDA hybrid polymers. Journal of Non-Crystalline Solids 353(16-17): 1598-1605 (2007).
Guillory et al., Glycidyl alkoxysilane 1-8 reactivities towards simple nucleophiles in organic media for improved molecular structure definition in hybrid materials. RSC ADV 6(78): 74087-74099 (2016).
Heidler et al., N-acyl-N-alkyl-sulfonamide anchors derived from Kenner's safety-catch linker: powerful tools in bioorganic and medicinal chemistry. Bioorg Med Chem 13(3):585-99 (2005).
International Application No. PCT/US17/25546 International Search Report and Written Opinion dated Sep. 6, 2017.
Legutki et al., Scalable high-density peptide arrays for comprehensive health monitoring., Nature Communications, Sep. 2014, 5:4785(7 pages).
March et al. Fetal Exposure to Moderate Ethanol Doses: Heightened Operant Responsiveness elicited by Ethanol-Related Reinforcers. Alcohol clin Exp Res 33(11):1981-1993.
Massimo, A. et al. Discovering sequence motifs in quantitative and qualitative peptide data. Technical University of Denmark. PhD Thesis. pp. 1-94 (Sep. 30, 2012).
Mateescu, A. et al. Thin Hydrogel Films for Optical Biosensor Applications, Membranes 2:40-69 (2012).
Naranbhai et al. Ratio of Monocytes to Lymphocytes in Peripheral Blood Identifies Adults at Risk of Incident Tuberculosis Among HIV-Infected Adults Initiating Antiretroviral Therapy. J Infect Dis 209(4):500-509 (2014).
Nieba, L. et al. Competition BIAcore for Measuring True Affinities: Large Differences from Values Determined from Binding Kinetics, Analytical Biochemistry, 234:155-165 (Feb. 15, 1996).

(56) References Cited

OTHER PUBLICATIONS

Perosa et al., Generation of biologically active linear and cyclic peptides has revealed a unique fine specificity of rituximab and its possible cross-reactivity with acid sphingomyelinase-like phosphodiesterase 3b precursor. Blood 107(3): 1070-1077 (2006).
Remesic et al., Cyclic Opioid Peptides. Curr Med Chem 23(13):1288-1303 (2016).
Schubert et al. The Mtb proteome library: a resource of assays to quantify the complete proteome of *Mycobacterium tuberculosis*. Cell Host Microbe 13(5):602-12 (2013).
Spengler et al., (Supplemental Materials) The synthesis of an EDTA-like chelating peptidomimetic building block suitable for solid-phase synthesis. Chem Commun 53: 2634-2636 (2017).
Spengler et al., The synthesis of an EDTA-like chelating peptidomimetic building block suitable for solid-phase synthesis. Chem Commun 53: 2634-2636 (2017).
U.S. Appl. No. 16/090,549 Non-Final Office Action dated Dec. 24, 2020.
U.S. Appl. No. 16/348,485 Non-Final Office Action dated May 26, 2021.
U.S. Appl. No. 16/968,512 Non-Final Office Action dated Jun. 14, 2021.
Wang et al., Optimization of RGD-Containing Cyclic Peptides against αvβ3 Integrin. Mol Cancer Ther. 15(2): 232-240 (2016).
Wrighton et al., Small Peptides as Potent Mimetics of the Protein Hormone Erythropoietin. Science, 273 (1996): 458-450.
Ingenito et al.: Efficient loading of sulfonamide safety-catch linkers by Fmoc amino acid fluorides. Org Lett. 4(7):1187-1188 (2002).
Yin at al: Acylsulfonamide safety-catch linker: promise and limitations for solid-phase oligosaccharide synthesis. Beilstein J Org Chem. 8:2067-2071 (2012).
Harris et al.: Synthesis of a C-Terminal Thioester Derivative of the Lipopeptide Pam2CSKKKKG Using Fmoc SPPS. Synlett 2007(5):0713-0716 DOI:10.1055/s-2007-970759 (2007).
Mohorcic et al.: Surface with antimicrobial activity obtained through silane coating with covalently bound polymyxin B. J Mater Sci Mater Med. 21(10):2775-2782 doi: 10.1007/s10856-010-4136-z (2010).
Triola et al.: Solid-phase synthesis of lipidated Ras peptides employing the Ellman sulfonamide linker. Chemistry 16(31):9585-9591 (2010).
Gandhiraman et al.: PECVD coatings for functionalization of point-of-care biosensor surfaces. Vacuum 86(5):547-555 (2012).
U.S. Appl. No. 16/348,485 Final Office Action dated Oct. 8, 2021.
EP Application No. 17870322.9 Extended European Search Report dated Apr. 17, 2020.
EP Application No. 17870436.7 Extended European Search Report dated Jul. 1, 2020.
U.S. Appl. No. 16/968,512 Final Office Action dated Mar. 10, 2023.
U.S. Appl. No. 16/968,512 Non-Final Office Action dated Sep. 15, 2022.
Aumelas, A et al. Formation of native disulfide bonds in endothelin-1. Structural evidence for the involvement of a highly specific salt bridge between the prosequence and the endothelin-1 sequence. Biochemistry vol. 37,15 (1998): 5220-30. doi: 10.1021/bi9723764.
U.S. Appl. No. 16/968,512 Office Action dated Sep. 22, 2023.

PL8 Molecule (HT960)

MALDI-MS (SSA) Measurement: Fraction Desired Yield

HT960_S4_modified with W oxidation, H-to-N conversion, E protective group and R manual integration

| AMINO ACID | LAYER 1 AVG YIELD (n=2) | MSRMNT. %CV |
|---|---|---|
| L | 0.90 | 0.57 |
| F | 0.84 | 2.11 |
| S | 0.84 | 5.10 |
| V | 0.84 | 2.95 |
| P | 0.80 | 2.52 |
| A | 0.79 | 0.70 |
| D | 0.76 | 1.04 |
| G | 0.73 | 2.68 |
| Y | 0.65 | 3.52 |
| N | 0.64 | 0.96 |
| Q | 0.53 | 0.95 |
| H | 0.52 | 2.19 |
| E | 0.41 | 4.44 |
| K | 0.40 | 8.14 |
| W | 0.15 | 5.38 |
| R | 0.01 | 0.23 |

Layer 1
Average Yield: 0.64

| AMINO ACID | LAYER 2 AVG YIELD (n=2) | MSRMNT. %CV |
|---|---|---|
| G | 1.00 | 0.00 |
| D | 1.00 | 0.00 |
| E | 1.00 | 0.00 |
| S | 1.00 | 0.00 |
| F | 1.00 | 0.00 |
| L | 0.99 | 0.09 |
| V | 1.00 | 0.00 |
| H | 1.00 | 0.00 |
| R | 1.00 | 0.00 |
| K | 1.00 | 0.00 |
| Q | 1.00 | 0.00 |
| N | 1.00 | 0.00 |
| W | 1.00 | 0.00 |
| A | 1.00 | 0.00 |
| Y | 1.00 | 0.00 |
| P | 1.00 | 0.00 |

Layer 2
Average Yield: 1.00

| AMINO ACID | LAYER 3 AVG YIELD (n=2) | MSRMNT. %CV |
|---|---|---|
| G | 1.00 | 0.00 |
| D | 1.00 | 0.00 |
| E | 1.00 | 0.00 |
| S | 1.00 | 0.00 |
| F | 1.00 | 0.00 |
| L | 1.00 | 0.00 |
| V | 1.00 | 0.00 |
| H | 1.00 | 0.00 |
| R | 1.00 | 0.00 |
| K | 1.00 | 0.00 |
| Q | 1.00 | 0.00 |
| N | 1.00 | 0.00 |
| W | 1.00 | 0.00 |
| A | 1.00 | 0.00 |
| Y | 1.00 | 0.00 |
| P | 1.00 | 0.00 |

Layer 3
Average Yield: 1.00

| AMINO ACID | LAYER 4 AVG YIELD (n=2) | MSRMNT. %CV |
|---|---|---|
| G | 1.00 | 0.00 |
| D | 1.00 | 0.00 |
| E | 1.00 | 0.00 |
| S | 1.00 | 0.00 |
| F | 1.00 | 0.00 |
| L | 1.00 | 0.00 |
| V | 1.00 | 0.00 |
| H | 1.00 | 0.00 |
| R | 1.00 | 0.00 |
| K | 1.00 | 0.00 |
| Q | 1.00 | 0.00 |
| N | 1.00 | 0.00 |
| W | 1.00 | 0.00 |
| A | 1.00 | 0.00 |
| Y | 1.00 | 0.00 |
| P | 1.00 | 0.00 |

Layer 4
Average Yield: 1.00

FIG. 3

MALDI-MS (SSA) Measurement: Fraction Desired Yield

HT962_S4_modified with W oxidation, H-to-N conversion, E protective group and R manual integration

| LAYER 1 | | | LAYER 2 | | | LAYER 3 | | | LAYER 4 | | |
|---|---|---|---|---|---|---|---|---|---|---|---|
| AMINO ACID | AVG YIELD (n=2) | MSRMNT. %CV | AMINO ACID | AVG YIELD (n=2) | MSRMNT. %CV | AMINO ACID | AVG YIELD (n=2) | MSRMNT. %CV | AMINO ACID | AVG YIELD (n=2) | MSRMNT. %CV |
| L | 0.90 | 2.79 | G | 1.00 | 0.00 | G | 1.00 | 0.00 | G | 1.00 | 0.00 |
| F | 0.84 | 3.73 | D | 1.00 | 0.00 | D | 1.00 | 0.00 | D | 1.00 | 0.00 |
| S | 0.82 | 0.04 | E | 1.00 | 0.00 | E | 1.00 | 0.00 | E | 1.00 | 0.00 |
| V | 0.82 | 2.91 | S | 1.00 | 0.00 | S | 1.00 | 0.00 | S | 1.00 | 0.00 |
| P | 0.80 | 1.31 | F | 1.00 | 0.00 | F | 1.00 | 0.00 | F | 1.00 | 0.00 |
| A | 0.76 | 6.00 | L | 0.99 | 0.09 | L | 1.00 | 0.00 | L | 1.00 | 0.00 |
| D | 0.69 | 13.25 | V | 1.00 | 0.00 | V | 1.00 | 0.00 | V | 1.00 | 0.00 |
| G | 0.67 | 0.50 | H | 1.00 | 0.00 | H | 1.00 | 0.00 | H | 1.00 | 0.00 |
| Y | 0.66 | 4.44 | R | 1.00 | 0.00 | R | 1.00 | 0.00 | R | 1.00 | 0.00 |
| N | 0.64 | 7.41 | K | 1.00 | 0.00 | K | 1.00 | 0.00 | K | 1.00 | 0.00 |
| Q | 0.55 | 6.12 | Q | 1.00 | 0.00 | Q | 1.00 | 0.00 | Q | 1.00 | 0.00 |
| H | 0.44 | 0.17 | N | 1.00 | 0.00 | N | 1.00 | 0.00 | N | 1.00 | 0.00 |
| E | 0.37 | 1.94 | W | 1.00 | 0.00 | W | 1.00 | 0.00 | W | 1.00 | 0.00 |
| K | 0.36 | 1.77 | A | 1.00 | 0.00 | A | 1.00 | 0.00 | A | 1.00 | 0.00 |
| W | 0.10 | 3.97 | Y | 1.00 | 0.00 | Y | 1.00 | 0.00 | Y | 1.00 | 0.00 |
| R | 0.01 | 37.62 | P | 1.00 | 0.00 | P | 1.00 | 0.00 | P | 1.00 | 0.00 |

Layer 1
Average Yield: 0.62

Layer 2
Average Yield: 1.00

Layer 3
Average Yield: 1.00

Layer 4
Average Yield: 1.00

Experimental

- Substrate: Si (<100> orientation) substrate containing ~250 nm thick thermal SiO$_2$
- Aminosilane coatings studied:
  ◦ 3-aminopropyltriethoxysilane (APTES)
  ◦ 3-aminopropylmethyldiethoxysilane (APDEMS)
  ◦ 3-aminopropyldiisopropylethoxysilane (APDIPES)
- Deposition method: Chemical vapor deposition using commercial CVD system
- Analytical characterization: Ellipsometry, WCA, XPS, AFM, Colorimetry, and MADLI-MS

FIG. 15

Why is Surface Properties Control Important?

- Surface properties impact
- Purity and number density of probes
- Non-specific interaction of biological molecules with the substrate
- Presentation of immobilized probes to biological molecules APTES and APDIPES Coatings are Most and Least Hydrophilic, Respectively

Side Chain Deprotection (SCD) Process

- 1ˢᵗ treatment
  - TFA : DMS : m-cresol : DODT : TfOH (0.49 : 0.29 : 0.10 : 0.02 : 0.10) at 0°C for 3 hrs.

- 2ˢᵗ treatment
  - TFA : thioanisole : DODT : TfOH (0.83 : 0.04 : 0.03 : 0.10) at RT for 1.5 hrs.

TFA: Trifluoroacetic acid
DMS: Dimethyl sulfide
TfOH: Trifluoromethanesulfonic acid
DODT: 2,2'-(Ethylenedioxy)diethanethiol

FIG. 20

Peptide Synthesis for Chemical Stability Study

- Preparatory synthesis
  - Aminosilane-coated surface was functionalized with tetramer peptide linker (GSGS).

- Main synthesis
  - A mixture of 9 amino acids (A, F, G, L, I, N, P, Q, and V) with no side chain protecting groups was coupled 12 times to create a diverse library of peptides.

- Synthesis was done on 8" oxide wafer (full field exposure). Small coupons were diced out of 8" wafer for analytical characterization.

FIG. 21

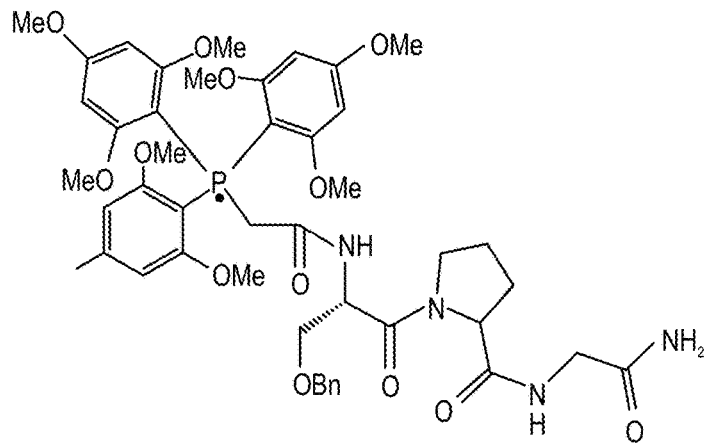
Exact mass:921.37
TMPP-SPG
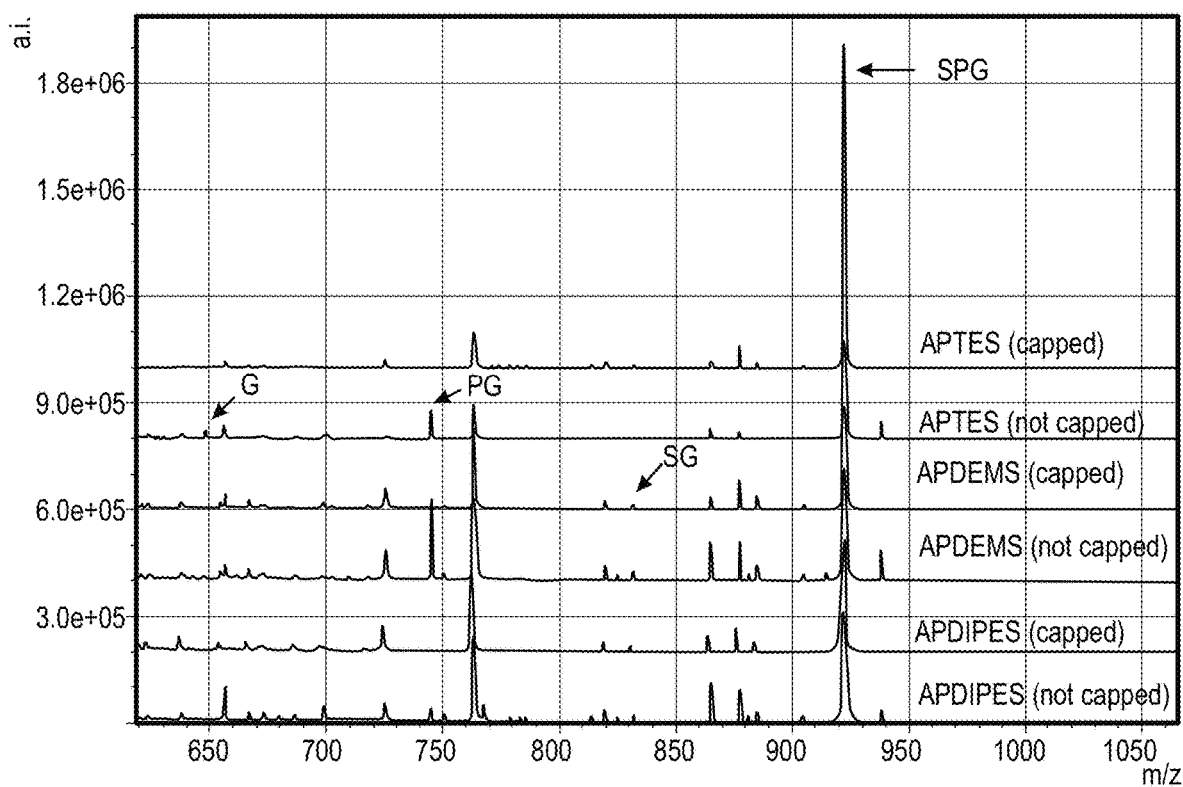
FIG. 29

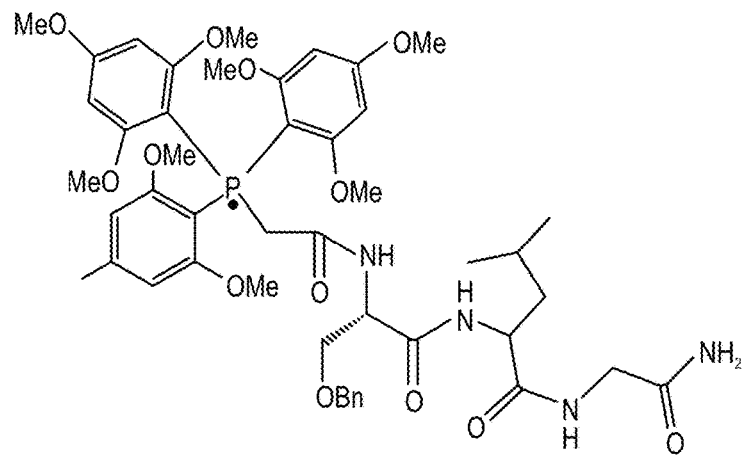
Exact mass:937.40
TMPP-SLG
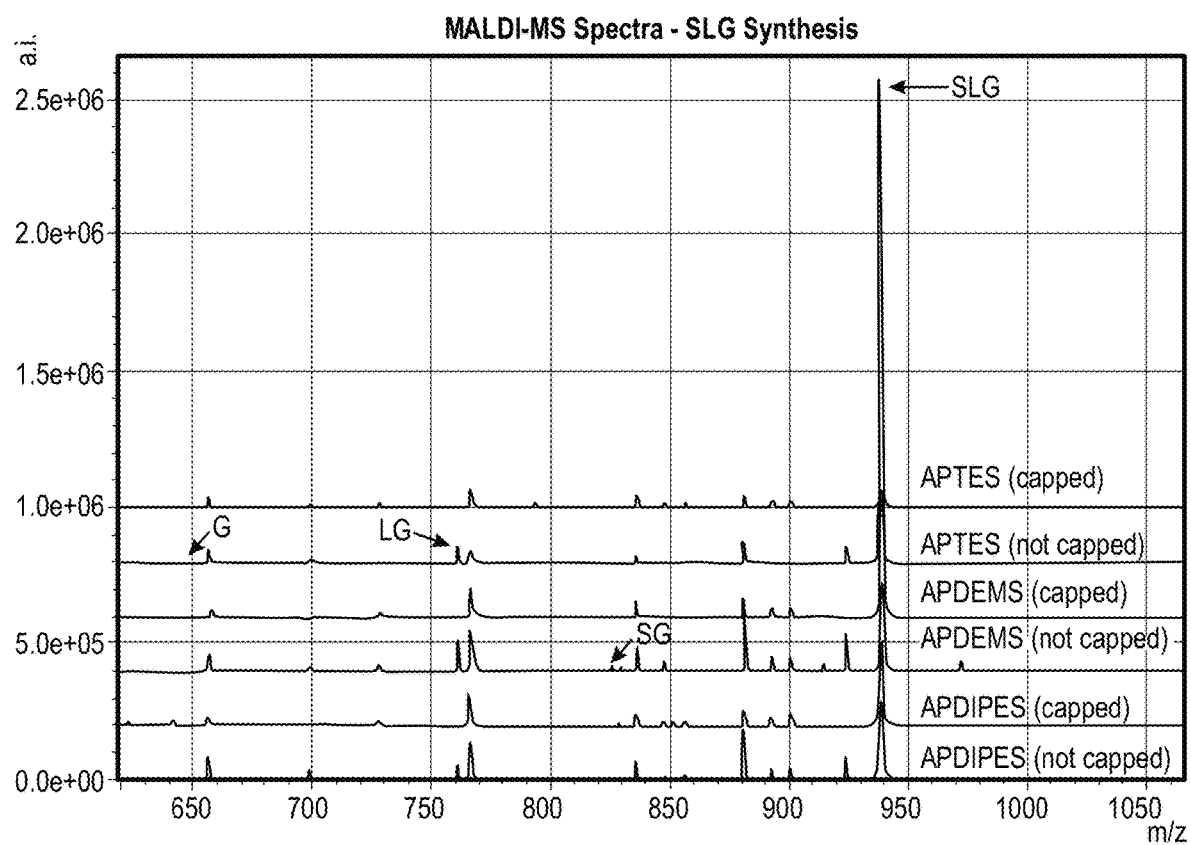
FIG. 31

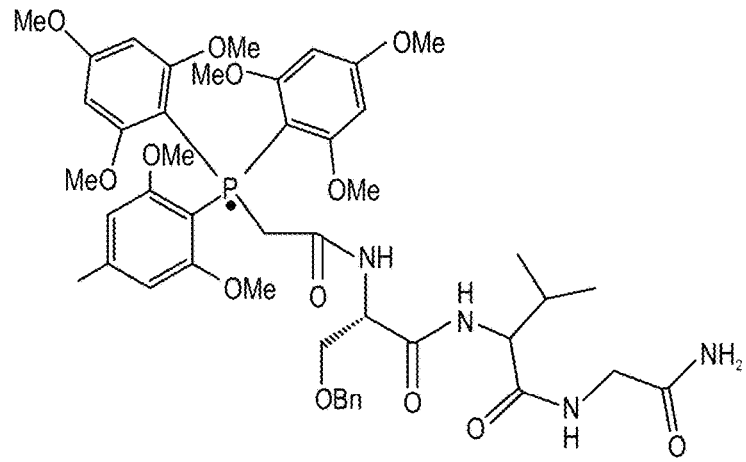
Exact mass:923.38
TMPP-SVG
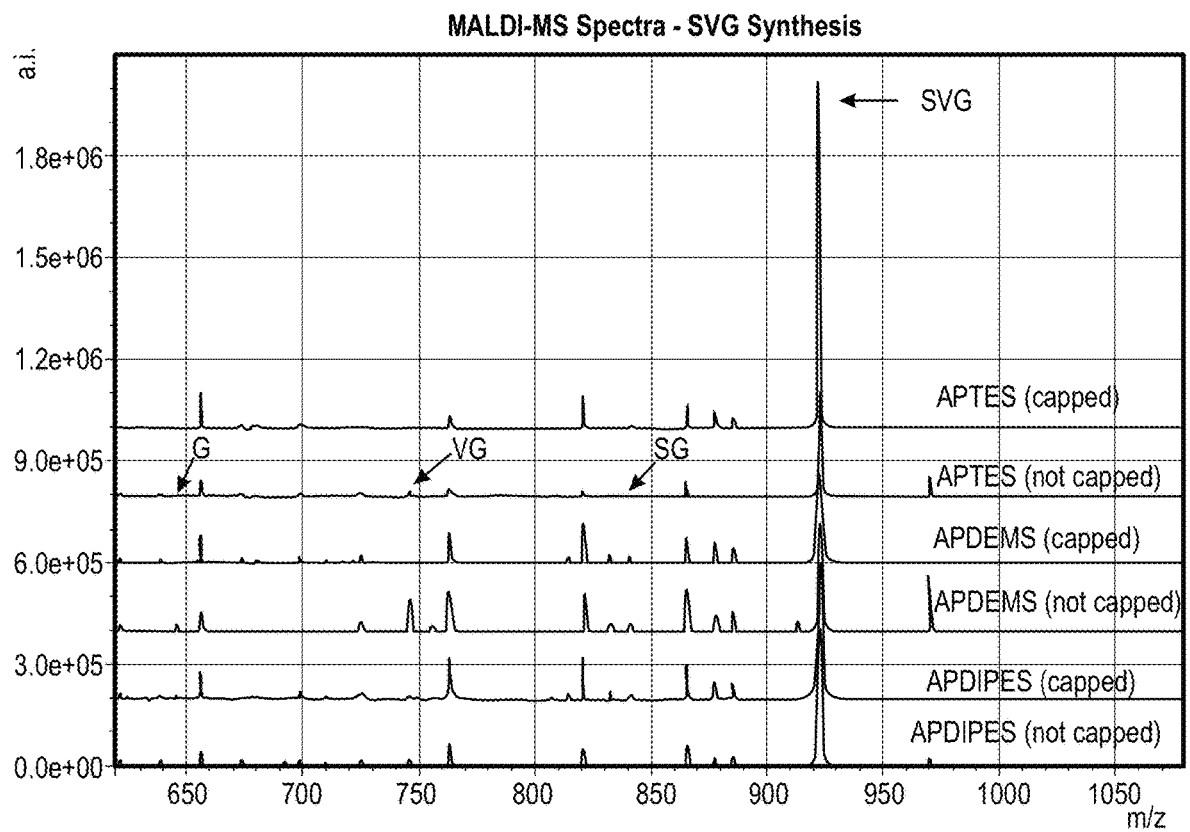
FIG. 33

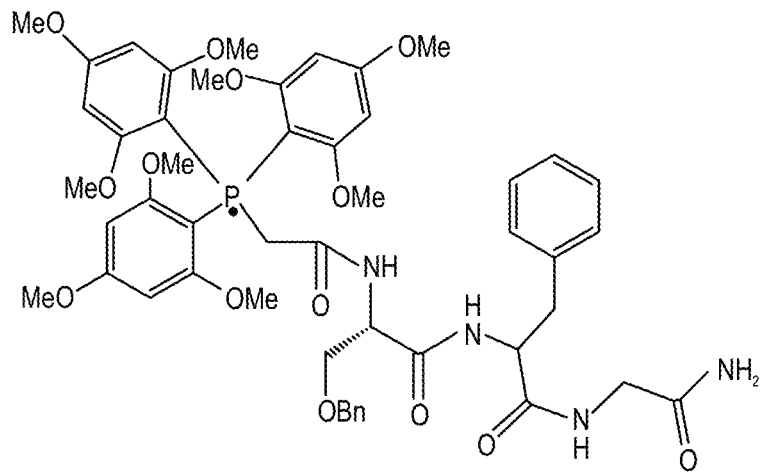
Exact mass:973.36
TMPP-SFG
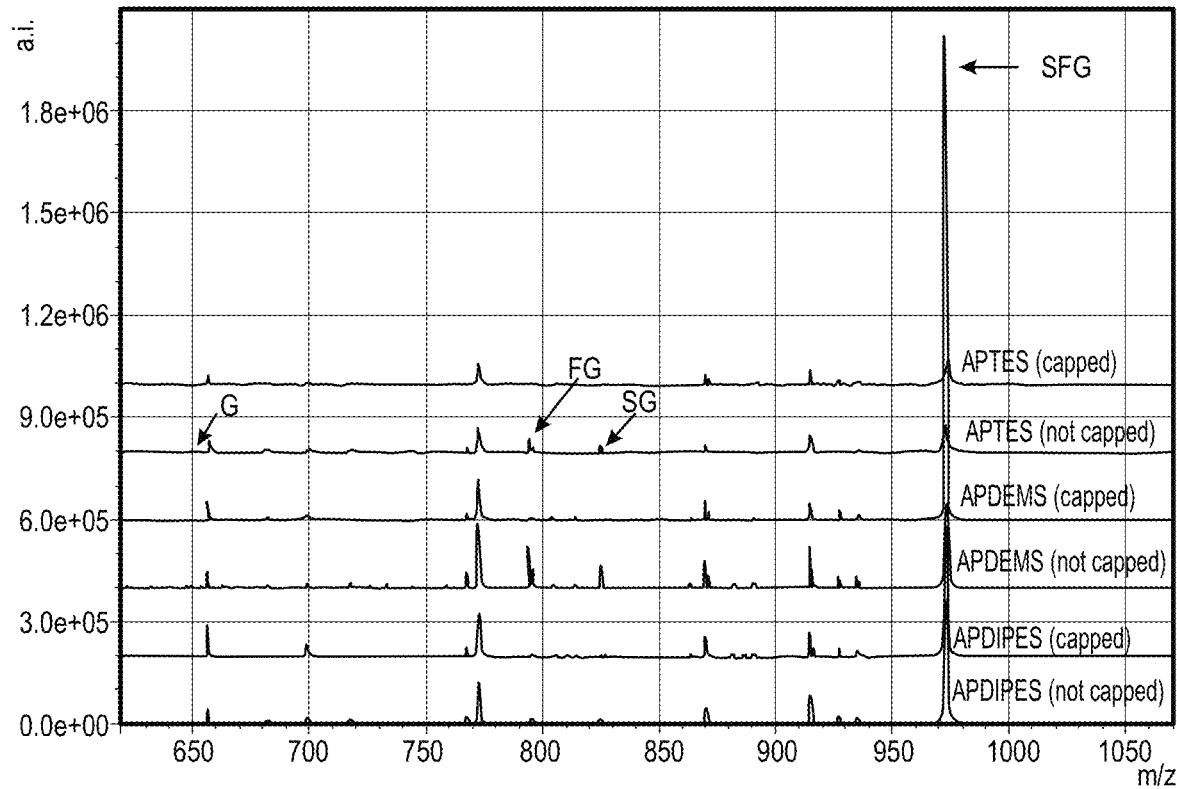
FIG. 35

FIG. 37

*Summary*

- Three aminosilanes yield coatings with comparable thickness but different hydrophilicity
- Hydrophilicity of the surface: APTES > APDEMS > APDIPES
- Nitrogen content of the coating is a function of number of ethoxy groups in aminosilane.
  - N content of aminosilane coating: APTES > APDEMS > APDIPES
- All aminosilanes generate smooth coatings.
- Chemical stability of peptide-functionalized aminosilane surface to SCD: APTES > APDEMS > APDIPES
- Acetic anhydride capping helps improve probe purity.
- APTES produces lowest percentage of pure probes. In general, APDIPES surface produces highest percentage of pure probes.

PRE-ASSEMBLED, PROTECTED, CHEMICALLY STABLE, CHEMOSELECTIVE LINKERS

CROSS-REFERENCE

This application is a U.S. National Phase of International Application No. PCT/US2017/060721, filed on Nov. 8, 2017, which claims the benefit of U.S. Provisional Application No. 62/419,861, filed Nov. 9, 2016, both of which are incorporated herein by reference in their entireties.

SUMMARY OF THE INVENTION

Disclosed herein are molecules having the structure:

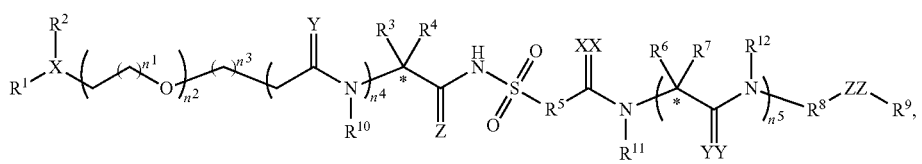

I or a salt thereof,
wherein $n^1$ can be independently 0, 1, 2, or 3;
$n^2$ can be 0, 1, 2, 3, 4, 5, 6, 7, 8, 9, 10, 11, 12, 13, 14, 15, 16, 17, 18, 19, or 20;
$n^3$ can be from 0, 1, 2, or 3;
$n^4$ can be 0 or 1; and
$n^5$ can be 0, 1, 2, or 3; and wherein
X can be O, N, or S;
Y, Z, XX, and YY can be the same or different and are independently O or S;
$R^1$ and $R^2$ can be the same or different and can be independently hydrogen, alkyl, alkenyl, aryl, heteroaryl, alkynyl, arylalkyl, arylalkenyl, haloalkyl, cycloalkyl, sulfonamidyl, acyl, electron lone pair, or —$CO_2R^{13}$, wherein $R^{13}$ can be alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they can be bound form a ring; or wherein $R^1$ or $R^2$ can comprise a nucleoside, nucleotide, polynucleotide, peptide, peptoid, saccharide, aptamer, or antibody or fragment thereof;
$R^3$, $R^4$, $R^6$, and $R^7$ are the same or different and can be independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;
$R^5$ can be alkyl, alkenyl, alkynyl or aryl, all optionally substituted with hydrogen, halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;
$R^8$, oriented from N to ZZ, can be alkyl, heteroalkyl, amino-substituted alkyl, amino-substituted heteroalkyl, amidoalkyl, amidoheteroalkyl, amino-substituted amidoheteroalkyl, each optionally substituted with an alkyl, heteroalkyl, amino-substituted alkyl, amino-substituted heteroalkyl, amidoalkyl, amidoheteroalkyl, or amino-substituted amidoheteroalkyl; or wherein $R^8$ is $\xi$—$(CR^{15}R^{16}CR^{17}R^{18})_m$—$\xi$, wherein m is 1 to 100, and $R^{15}$, $R^{16}$, $R^{17}$, and $R^{18}$ can be the same or different and are independently hydrogen, halo, alkyl, heteroalkyl, amino-substituted alkyl, amino-substituted heteroalkyl, amidoalkyl, amidoheteroalkyl, amino-substituted amidoheteroalkyl; or wherein $R^8$ can be

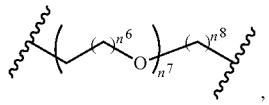

, wherein $n^6$ and $n^8$ can be the same or different and can be independently 1, 2, or 3, and $n^8$ can be 1 to 20;
$R^9$ can be an alkyl, heteroalkyl, hydroxyheteroalkyl, silylalkyl, siloxyalkyl siloxyheteroalkyl, siloxyhydroxyheteroalkyl, or wherein $R^9$ can be $R^{19}$—$(CH_2)_3$—Si$(Z)_p$, wherein p can be from 1 to 3, wherein Z can be selected from halo or alkoxy, and wherein $R^{19}$ can be selected from a hydroxyalkyl or carbamate;
$R^{10}$, $R^{11}$, and $R^{12}$ are the same or different and can be independently selected from hydrogen or alkyl; and wherein $R^9$ can be optionally linked to a solid phase;
ZZ is $NR^{20}$, O, S, or Se, wherein $R^{20}$ can be hydrogen or alkyl; and
(*) is a carbon center, wherein said carbon center can be independently a stereogenic center or a non-stereogenic center.

In some aspects are molecules or salts of structure I, wherein X can be N, and wherein $R^1$ and $R^2$ can be the same or different and can be independently selected from hydrogen, acyl, acyloxy, benzyl, triphenylmethyl, benzylidenyl, or p-toluenesulfonyl. In some aspects are molecules or salts of structure I, wherein the solid phase can comprise a substrate, a bead, or a chromatographic packing material. In some aspects are molecules or salts of structure I, wherein either of $R^3$ and $R^4$ can comprise a $C_1$-$C_{10}$ alkyl, cycloalkyl, aryl, or heteroaryl side chain. In one aspect are molecules or salts of structure I, wherein either of $R^3$ and $R^4$ can comprise a functional group that is at least partially protonated at a pH of about 7.3. In some aspects are molecules or salts of structure I, wherein either of $R^3$ and $R^4$ can comprise a functional group that is at least partially deprotonated at a pH of about 7.3. In some aspects are salts or molecules of structure I, wherein said side chain can comprise an amide, alcohol, or thiol. In one aspect are molecules or salts of structure I, wherein $R^3$ and $R^4$ can be hydrogen. In some aspects are molecules or salts of structure I, wherein either of $R^6$ and $R^7$ can comprise a $C_1$-$C_{10}$ alkyl, cycloalkyl, aryl, or heteroaryl side chain. In some aspects are molecules or salts of structure I, wherein either of $R^6$ and $R^7$ can comprise a functional group that is at least partially protonated at a pH of about 7.3. In some aspects are molecules or salts of structure I, wherein either of $R^6$ and $R^7$ can comprise a functional group that is at least partially deprotonated at a pH of about 7.3. In some aspects are molecules or salts of structure I, wherein a side chain can comprise an amide, alcohol, or thiol. In some aspects are molecules or salts of structure I, wherein $R^6$ and $R^7$ can be hydrogen.

Molecules of formula I will include the molecule having the structure:

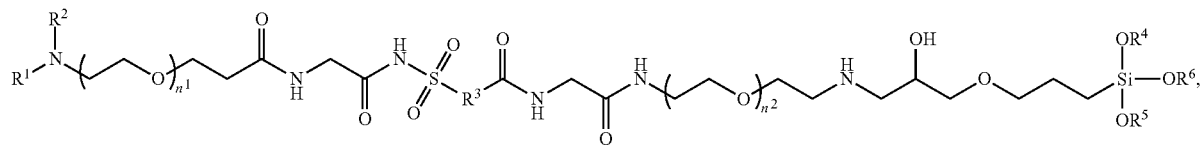

IA or a salt thereof,
wherein $n^1$=1-15 and $n^2$=1-6; and
wherein $R^1$ and $R^2$ can be the same or different and are independently hydrogen or acyloxy;
$R^3$ can be alkyl, alkenyl, alkynyl or aryl, all optionally substituted with 1, 2, 3, or 4 groups selected from hydrogen, halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl; and
$R^4$, $R^5$, and $R^6$ can be the same or different and are independently selected from hydrogen, alkyl, silyl, or siloxy.

In some aspects are molecules or salts of structure IA, wherein $R^3$ can be p-phenyl. In some aspects are molecules or salts of structure IA, wherein $R^3$ can be n-propyl. In some aspects are molecules or salts of structure I or IA, wherein $R^1$ or $R^2$ can comprise a peptide. In some aspects, the molecule or salt of structure I or IA can comprise a peptide. In one aspect, a peptide can comprise from 2 to 100 amino acids.

Also disclosed herein are arrays comprising the molecules or salts of structure I or IA. In one aspect, an array can comprise a peptide. In one aspect, an array can comprise at least 10,000 peptides per square centimeter. In one aspect, an array can comprise at least 300,000 peptides per square centimeter. In one aspect, an array can comprise at least 1 million peptides per square centimeter. In some aspects, an array can comprise a binding moiety. A binding moiety can comprise a nucleoside, nucleotide, polynucleotide, peptide, peptoid, saccharide, polysaccharide, aptamer, or antibody or fragment thereof. In some aspects, an array can comprise a fatty acid. A fatty acid can be fluorinated. Also disclosed herein are methods for the synthesis of arrays comprising the molecules or salts of structure I or IA. In one aspect, making an array comprises associating the molecules or salts of structure I or IA with a substrate. A substrate can be a silicon or silicon oxide wafer. In one aspect, an array can comprise at least 10,000 peptides per square centimeter. In one aspect, an array can comprise at least 300,000 peptides per square centimeter. In one aspect, an array can comprise at least 1 million peptides per square centimeter.

Also disclosed herein is a method. In some aspects, the method can comprise forming a solid support. Forming a solid support can comprise associating the solid support with molecules or salts of structures I or IA. A solid support can be a substrate, bead, polymer, or a chromatographic packing material.

Also disclosed herein is a use of the molecules or salts of structures I or IA for binding a nucleotide, polynucleotide, polypeptide, aptamer, or antibody or fragment thereof. Also disclosed herein is a use of the molecules or salts of structures I or IA for binding proteins or antibodies. Also disclosed herein is a method comprising binding a binding moiety to the molecules or salts of structures I or IA. In some aspects, the method can comprise identifying a binding moiety. Identifying can comprise an immunofluorescence assay. In some aspects, the binding moiety can comprise a nucleotide, polynucleotide, polypeptide, aptamer, or antibody or fragment thereof. In some aspects, the binding moiety can be obtained from a subject. In some aspects, the method can comprise determining the likelihood that the subject has a disease or a condition. A subject can be a human. In some aspects, a disease or condition can be an autoimmune disease, an infection, or cancer. In some aspects an autoimmune disease can be lupus, ulcerative colitis, Crohn's disease, or rheumatoid arthritis. In some aspects, an infection can be bacterial, viral, fungal, or parasitic. In some cases, the method further can comprise communicating a result via a communication medium.

Also disclosed herein is a method comprising cleaving a bond in the molecules or salts of structures I or IA. In some aspects, a bond can be the C—N bond of an N-acylsulfonamide. In some aspects, cleaving can comprise a first activating step and a second cleavage step. In some aspects, a first activating step can comprise alkylating an N-acylsulfonamide. In some aspects, alkylating can comprise use of an alkylating agent. In some aspects, an alkylating agent can be a diazo compound or alkyl halide. In some aspects, an alkylating agent can be diazomethane, methyl iodide, or iodoacetonitrile. In some aspects, the cleavage can comprise a vapor phase cleavage reaction. In some aspects, the cleavage can comprise a vapor-phase ammonia cleavage reaction.

Also disclosed herein are kits. In some aspects, the kits can comprise the molecules or salts of structures I or IA. In some cases a kit can comprise instructions for use. Also disclosed herein are methods of making a kit disclosed herein.

Also disclosed herein is a molecule having the structure:

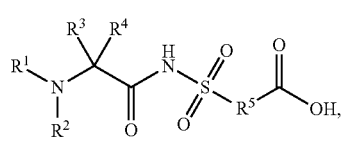

II or a salt thereof, wherein:
- $R^1$ and $R^2$ can be the same or different and are independently hydrogen, alkyl, alkenyl, aryl, heteroaryl, alkynyl, arylalkyl, arylalkenyl, haloalkyl, cycloalkyl, sulfonamidyl, acyl, electron lone pair, or —$CO_2R^6$, wherein $R^6$ can be alkyl, alkenyl, aryl, arylalkyl, arylalkenyl, haloalkyl, cycloalkyl, cycloalkylalkyl, or arylcycloalkylalkyl; or wherein $R^1$ and $R^2$ and the N to which they can be bound form a ring;
- $R^3$, $R^4$ can be the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; and
- $R^5$ can be alkyl, alkenyl, alkynyl or aryl, each optionally substituted with hydrogen, halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl.

In some aspects are molecules or salts of structure II, wherein $R^1$ and $R^2$ can be the same or different and are independently hydrogen, acyl, acyloxy, phthalimidyl, benzyl, triphenylmethyl, benzylidenyl, or p-toluenesulfonyl. In some aspects are molecules or salts of structure II, wherein either of $R^3$ and $R^4$ can comprise a $C_1$-$C_{10}$ alkyl, cycloalkyl, aryl, or heteroaryl side chain. In some aspects are molecules or salts of structure II, wherein either of $R^3$ and $R^4$ can comprise a functional group that is at least partially protonated at a pH of about 7.3. In some aspects are molecules or salts of structure II, wherein either of $R^3$ and $R^4$ can comprise a functional group that is at least partially deprotonated at a pH of about 7.3. In some aspects, a side chain can comprise an amide, alcohol, or thiol. In some aspects are molecules or salts or structure II, wherein $R^3$ and $R^4$ can be hydrogen.

The compound of structure II includes the structures:

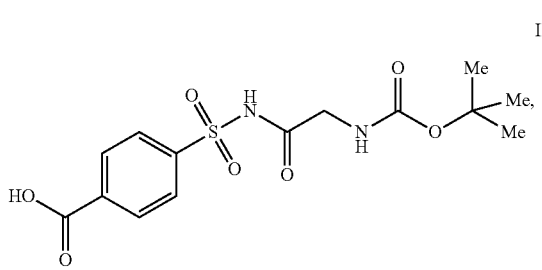

IIA

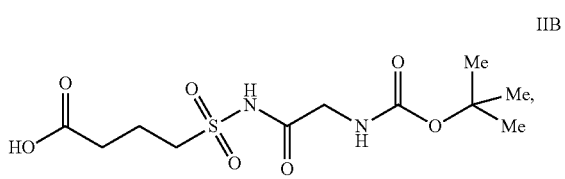

IIB or salts thereof.

The compound of structure II includes the structures:

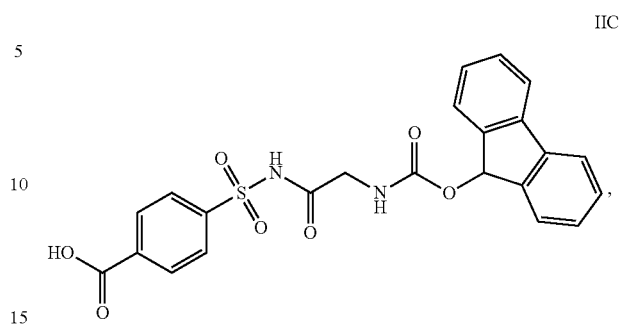

IIC

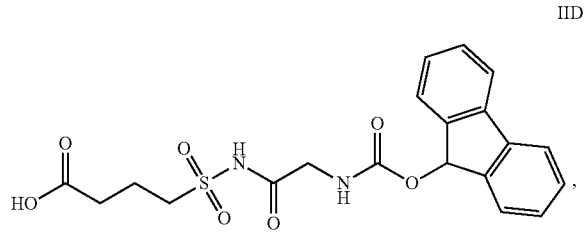

IID or salts thereof.

Also disclosed herein is a method for synthesizing molecules. In some aspects, the method can comprise forming molecules with the compounds of structures IIA, IIB, IIC, or IID. In some aspects, the method can comprise coupling the compounds of structures IIA, IIB, IIC, or IID to an amino group on a solid phase. In some aspects, the method can further comprise deprotecting the compounds of structures IIA, IIB, IIC, or IID to form a second amino group. In some aspects, a solid phase can be a substrate, a bead, a polymer, or a chromatographic packing material. In some aspects, a deprotection can comprise a photoacid or a photoacid generator. In some aspects, a deprotection can comprise a photobase or a photobase generator. In some aspects, the method further can comprise an amine capping step. In some aspects, the amine capping step can be performed after the coupling step, and before the deprotection step. In some aspects, the amine capping step can comprise reacting the first amino group with a capping agent. In some aspects, the capping step can form an alkylamine, arylamine, acetamide, carbamate, phthalimide, enamine, sulfonamide, or N-protected amino acid. In some aspects, the protected amino acid can be an N-acyl-protected amino acid. In some aspects, the protected amino acid can be acetylglycine. In some aspects, the capping agent can be acetic anhydride, acetyl chloride, acetyl fluoride, or an acylglycine. Also disclosed herein are molecules made by the process of the any of the disclosed methods.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 3. depicts MALDI analysis and coupling yields for step-wise coupling of tetrapeptides to a PL8 Molecule: HT960.

FIG. 4. depicts MALDI analysis and coupling yields for step-wise coupling of tetrapeptides to a PL8 Molecule: HT963.

FIG. 11 depicts substrate characteristics, coating compositions, deposition methods, and analytical characterization methods

FIG. 15 depicts why surface properties control important.

FIG. 20 depicts an experimental process for side chain deprotection.

FIG. 21 depicts an outline of a peptide synthesis process.

FIG. 29 depicts a MALDI-MS analysis of array coatings.

FIG. 31 depicts a MALDI-MS analysis of array coatings.

FIG. 33 depicts a MALDI-MS analysis of array coatings.

FIG. 35 depicts a MALDI-MS analysis of array coatings.

FIG. 37 depicts a summary of amino coating properties.

DETAILED DESCRIPTION

Figure 1:
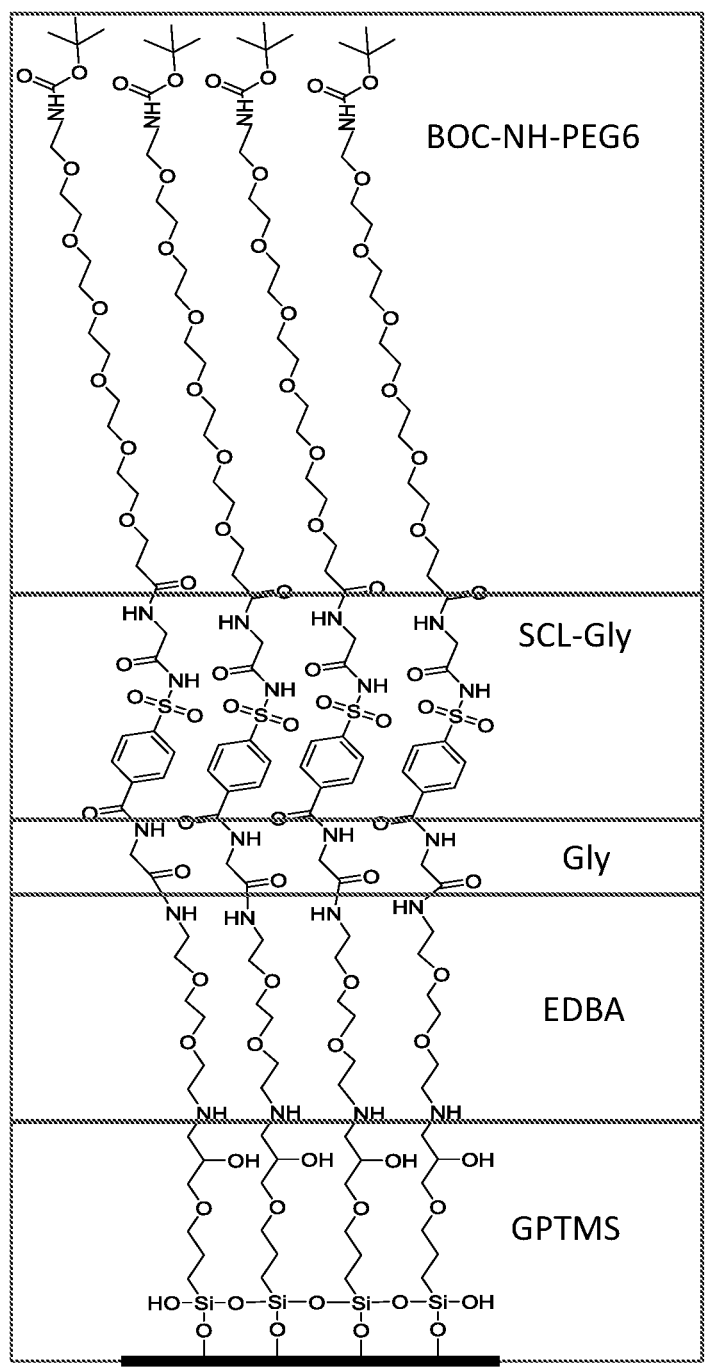
FIG. 1. depicts a molecule structure according to structure I. SCL-Gly is safety-catch-glycine. Gly is glycine. EDBA is (ethylenedioxy)bis(ethylamine). GPTMS is 3-glycidoxypropyltrimethoxysilane.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to +10%. In some embodiments, the term "about" refers to +5%.

Overview

Detecting and diagnosing immune-mediated disorders, including autoimmune disorders, infections, and cancer, is challenging, with patients having a difficult time receiving an accurate or correct diagnosis. In many instances, patients are often misdiagnosed with other autoimmune conditions because of the closely related nature of these diseases. The disclosure, in one aspect, relates to compounds, methods, and devices that identify differential patterns of peripheral-blood antibody binding to a array-bound molecular library. Differential binding of patient samples to the array results in specific binding patterns or signatures indicative of the disease state of the patient. These binding signatures can accurately determine or diagnose a disease activity, including but not limited to autoimmune disease activity, infectious disease activity, cancer activity, and diabetes disease activity. The identification of such differential binding activity, or signature, is referred to as "immunosignaturing." Synthesized peptide libraries have been commonly used for antibody binding characterization. However, protein and robotically printed peptide arrays have been cost-prohibitive and in situ synthesized peptide arrays have suffered from lack of scalability, poor reproducibility and low production quality. The technologies herein, in one aspect, will enable reliable, low cost, and scaleable methods for construction and use of arrays for immunosignaturing assays.

In some embodiments, arrays with chemical libraries produced by the technologies disclosed herein are used for immune-based diagnostic assays, for example, immunosignature assays. In one aspect, using a patient's antibody repertoire from a drop of blood bound to the arrays, a fluorescence binding profile image of the bound array provide sufficient information to identify and classify a disease state. The arrays disclosed herein incorporate analytical measurements capability within each synthesized array using orthogonal analytical methods including ellipsometry, mass spectrometry, and fluorescence. These measurements enable longitudinal qualitative and quantitative assessment of array synthesis performance.

In some embodiments, detection of antibody binding on a peptide array poses some challenges that can be addressed by the technologies disclosed herein. The technologies disclosed herein address two potential shortcomings of using molecular arrays to profile antibody binding. First, non-specific antibody binding on a array is minimized by coating the solid support with a moderately hydrophilic monolayer comprising, in some embodiments, polyethylene glycol. In some embodiments, the hydrophilic monolayer is homogeneous. Second, synthesized library are linked to the surface using a linker that moves the peptide away from the surface of the solid support so that the peptide may be presented to an antibody in an unhindered orientation. The technologies disclosed herein include such linkers, which, in one aspect, connect chemical libraries to solid supports, including, in some aspects, arrays for immunosignaturing.

The synthesis of linkers by iterative coupling of linker subunits has limitations when certain functional groups are incorporated into the linker. As an example, sulfonamides exhibit poor reactivity in peptide coupling reactions. When linkers contain sulfonamide-terminated subunits, the reaction between the nitrogen of the sulfonamide and the carboxylic acid of the next subunit of the linker is slow, requiring elevated reaction times and temperatures to achieve even mediocre reaction of the sulfonamide. Residual, unreacted sulfonamides present the problem that, while less reactive than primary amines, they will still exhibit reactivity as peptide synthesis progresses. In subsequent coupling steps, undesired coupling of initially unreacted sulfonamides leads ultimately to truncation and deletion products in the final synthesized linker products. Furthermore, poor reactivity lowers the overall yield of final synthesized linker products. Furthermore, the poor reactivity of sulfonamides in coupling reactions is exacerbated in coupling performed on solid phase systems, because the chemical sensitivity of the solid phase prevents aggressive reaction conditions required to force coupling reactions to completion. In one aspect, disclosed herein, the problem of poor sulfonamide reactivity under standard peptide coupling conditions is overcome by the coupling of pre-assembled sulfonamide-amino building blocks. In one aspect, the pre-assembled sulfonamide-amino building blocks comprise a first moiety comprising a sulfonamide functional group at a first end, and a carboxylic acid functional group at a second end. In one aspect, the pre-assembled sulfonamide-amino building block comprises a second moiety comprising a C=O functional group at a first end, covalently bound at the carbon to the nitrogen of the sulfonamide functional group, and an amino group at a second end. In one aspect, the amino group is protected. In one aspect the amino group is protected as a tert-butyl carbamate (Boc)-protected amine or as a 9-fluorenylmethyl carbamate (Fmoc)-protected amine.

Further disclosed herein are arrays comprising the molecules disclosed herein. In some aspects, the arrays comprise a nucleoside, nucleotide, polynucleotide, peptide, peptoid, saccharide, aptamer, lipid, lipo-peptide, or antibody or fragment thereof chemically bound to the linker. In one aspect, the nucleoside, nucleotide, polynucleotide, peptide, peptoid, saccharide, aptamer, or antibody or fragment thereof comprise a chemical library. In some embodiments, the array is a peptide array. In some aspects, the peptide array is synthesized in situ.

One of the major deficiencies of in situ synthesized peptide arrays has been the inability to directly measure purity of the synthesized peptide features. In some embodiments, the technologies include qualitative in situ mass spectrometry of synthesized peptides directly from solid support. Mass spectrometry is performed by incorporating a gas-phase cleavable linker between the solid support and the synthesized peptides so that cleavage of the peptide is done without diffusion from the array feature. Following peptide cleavage, Matrix-Assisted Laser Desorption Ionization (MALDI) mass spectrometry is performed directly on the solid support by applying a thin aerosol matrix layer and subsequently focusing the MALDI laser on individual peptide features to acquire a mass spectrum for each synthesized peptide. Qualitative in situ MALDI mass spectrum from a peptide array feature produced using the photolithographic synthesis approach are also included in the methods and devices described herein. Other analyses known to those of skill in the art may also be used to quantify and/or qualify the fidelity of the in situ synthesis process disclosed herein.

In one aspect, the use of a pre-assembled sulfonamide-amino building block reduces background autofluorescence of the synthesized linker associated with heating the surface of a solid phase in the presence of solvent, base, and peptide coupling reagents. In one aspect, the use of a pre-assembled sulfonamide-amino building block increases fidelity of the overall peptide coupling-based linker synthesis. In one aspect, the synthesized linkers further comprise a nucleoside, nucleotide, polynucleotide, peptide, peptoid, saccharide, aptamer, or antibody or fragment thereof. In one aspect, the incorporation of a sulfonamide into linkers allows for cleavage of the linker. In one aspect, cleavage of the linker further comprises analysis of the nucleoside, nucleotide, polynucleotide, peptide, peptoid, saccharide, aptamer, or antibody or fragment thereof. In some aspects, analysis of the peptide can comprise liquid chromatography or gas chromatography. In some aspects, the analysis comprises spectroscopic or spectrometric analysis. In some embodiments, spectrometric analysis is Matrix-assisted laser desorption/ionization spectrometry (MALDI). In one aspect, the incorporation of a sulfonamide linkers provides a site for cleavage that is chemically stable to the conditions for cleaving protected functional groups on the nucleoside, nucleotide, polynucleotide, peptide, peptoid, saccharide, aptamer, or antibody or fragment thereof. In one aspect, linkers are analyzed by ellipsometry.

Definitions

The terms "attach", "bind", "couple", and "link" are used interchangeably and refer to covalent interactions (e.g., by chemically coupling), or non-covalent interactions (e.g., ionic interactions, hydrophobic interactions, hydrogen bonds, hybridization, etc.). The terms "specific", "specifically", or "specificity" refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule and any one of the plurality of other molecules). For example, two molecules may be specifically attached, specifically bound, specifically coupled, or specifically linked. Furthermore, "binding" may refer to either a specific interaction, such as the interaction of an antibody with an epitope, or it may refer to a non-specific interaction.

Nomenclature

Unless otherwise indicated, the term "alkyl" as employed herein alone or as part of another group can include both straight and branched chain hydrocarbons, containing, for instance, 1 to 20 carbons, 1 to 10 carbons, or 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxyl, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl ano/or alkylthio.

Unless otherwise indicated, the term "cycloalkyl" as employed herein alone or as part of another group can include saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl, adamantyl, and the like, any of which may be optionally substituted with 1 to 4 substituents such as halogen, alkyl, alkoxy, hydroxyl, aryl, aryloxy, arylalkyl, cycloalkyl, hydroxyalkyl, alkylamido, alkanoylamino, oxo, acyl, arylcarbonylamino, amino, nitro, cyano, thiol and/or alkylthio and/or any of the substituents for alkyl.

The term "alkanoyl" as used herein alone or as part of another group can refer to alkyl linked to a carbonyl group.

Unless otherwise indicated, the term "alkenyl" as used herein by itself or as part of another group can refer to straight or branched chain radicals of, for instance, 2 to 20 carbons in the normal chain, which include one to six double bonds in the normal chain, such as vinyl, 2-propenyl, 3-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxyl, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "alkynyl" as used herein by itself or as part of another group can refer to straight or branched chain radicals of 2 to 20 carbons in the normal chain, which include one triple bond in the normal chain, such as 2-propynyl, 3-butynyl, 2-butynyl, 4-pentynyl, 2-hexynyl, 3-hexynyl, 2-heptynyl, 3-heptynyl, 4-heptynyl, 3-octenyl, 3-nonenyl, 4-decenyl, 3-undecenyl, 4-dodecenyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxyl, alkanoylamino, alkylamido, arylcarbonylamino, nitro, cyano, thiol, and/or any of the alkyl substituents set out herein.

The term "halogen" or "halo" as used herein alone or as part of another group can refer to chlorine, bromine, fluorine, and iodine, as well as $CF_3$.

Unless otherwise indicated, the term "aryl" as employed herein alone or as part of another group can refer to monocyclic and biclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, halolalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxyl, nitro, cyano, amino, substituted amino wherein the amino can include 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonyloxy, arylcarbonylamino, arylsulfinyl, arylsulfinylalkyl, arylsulfonylamino or arylsulfonaminocarbonyl and/or any of the alkyl substituents set out herein.

Unless otherwise indicated, the term "amino-substituted" as employed herein alone or as part of another group can refer to a chemical group having from 1 to 10 amino groups substituted thereon.

Unless otherwise indicated, the term "alkylthio" (also known as "thioalkyl") or "arylthio" (also known as "thioaryl") as employed herein alone or as part of another group can include any of the above alkyl or aryl groups linked to a sulfur atom.

Unless otherwise indicated, the term "selenoalkyl" as employed herein alone or as part of another group can include any of the above alkyl groups linked to a selenium atom.

Unless otherwise indicated, the term "alkylamino" or "arylamino" as employed herein alone or as part of another group can include any of the above alkyl or aryl groups linked to a nitrogen atom.

Unless otherwise indicated, the term "acyl" as employed herein by itself as part of another group, as defined herein, can refer to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group can refer to a 5-, 6-, or 7-membered saturated or partially unsaturated ring which can include 1 to 2 heteroatoms such as nitrogen, oxygen and/or sulfur, linked through a carbon atom or a heteroatom, where possible, optionally via the linker $(CH_2)_r$ (where r is 1, 2, or 3).

Unless otherwise indicated, the term "heteroaryl" as used herein alone or as part of another group can refer to a 5- or 6-membered aromatic ring which can include 1, 2, 3 or 4 heteroatoms such as nitrogen, oxygen or sulfur, and such rings fused to an aryl, cycloalkyl, heteroaryl or cycloheteroalkyl ring, and includes possible N-oxides. The heteroaryl group may optionally include 1 to 4 substituents such as any of the substituents set out above for alkyl.

Unless otherwise indicated, the term "heteroalkyl" as used herein alone or as part of another group can refer to an alkyl group, as defined herein, which can include 1, 2, 3, or 4 heteroatoms such as nitrogen, oxygen or sulfur. The heteroalkyl group may optionally include 1 to 4 substituents such as any of the substituents set out above for alkyl.

All stereoisomers of compounds are contemplated, either in admixture or in pure or substantially pure form. Compounds can have asymmetric carbon centers at any of the carbon atoms including any one of the R substituents. Compounds can be either optically active or optically inactive. Asymmetric carbon centers can be independently in an R- or S-configuration. As defined herein asymmetric carbons are carbons that are a stereogenic center. Consequently, compounds of structures I, IA, or II can exist in enantiomeric or diastereomeric forms or in mixtures thereof. Enantiomeric mixtures can exist with an enantiomeric excess of 10%, 20%, 30%, 40%, 50%, 60%, 70%, 80%, 85%, 90%, 95%, 96%, 97%, 98%, 99%, 99.5% or 100%. Diastereomeric mixtures can exist with a diastereomeric ratio of 1:1, 2:1, 3:1, 4:1, 5:1, 6:1, 7:1, 8:1, 9:1, 10:1, 20:1, 50:1, 100:1, or 500:1. The processes for preparation of the molecules disclosed herein can utilize racemates, enantiomers or diastereomers as starting materials. When diastereomeric or enantiomeric products are prepared, they can be separated by conventional methods, for example, by chromatographic or fractional crystallization.

A polynucleotide, as used herein, can be any type of nucleic acid molecule, including DNA, RNA, a hybridization thereof, or any combination thereof. For example, a polynucleotide can be cDNA, genomic DNA, mRNA, tRNA, rRNA, or microRNA.

A peptide, polypeptide, or protein can be contemplated to include any fragments thereof, in particular, immunologically detectable fragments. A peptide can be contemplated to include an α-peptide, a β-peptide, or a γ-peptide.

Supports/Substrates/Solid Phases

The present disclosure provides solid supports (also known as solid phases, substrates, or supports). The nature and geometry of a support or substrate can depend upon a variety of factors, including the type of array (e.g., one-dimensional, two-dimensional or three-dimensional). Generally, a substrate can be composed of any material which will permit coupling of a nucleoside, nucleotide, polynucleotide, peptide, peptoid, saccharide, aptamer, or antibody or fragment thereof, which will not melt or degrade under the conditions used to couple said nucleoside, nucleotide, polynucleotide, peptide, peptoid, saccharide, aptamer, or antibody or fragment thereof to said solid support. A solid support can be composed of any material which will permit coupling of a target analyte, and/or other moiety at one or more discrete regions and/or discrete locations within the discrete regions. A solid support can be composed of any material which will permit washing or physical or chemical manipulation without dislodging a target analyte or binding moiety from the solid support.

A substrate may take a variety of configurations ranging from simple to complex, depending on the intended use of the array. Thus, a substrate can have an overall slide or plate configuration, such as a rectangular or disc configuration. A standard microplate configuration can be used. In some embodiments, the surface may be smooth or substantially planar, or have irregularities, such as depressions or elevations. For example, the substrates of the presently disclosed subject matter can include at least one surface on which a pattern of recombinant virion microspots can be coupled or deposited. In some instances, a substrate may have a rectangular cross-sectional shape, having a length of from about 10-200 mm, 40-150 mm, or 75-125 mm; a width of from about 10-200 mm, 20-120 mm, or 25-80 mm, and a thickness of from about 0.01-5.0 mm, 0.1-2 mm, or 0.2 to 1 mm.

A support may be organic or inorganic; may be metal (e.g., copper or silver) or non-metal; may be a polymer or nonpolymer; may be conducting, semiconducting or non-conducting (insulating); may be reflecting or nonreflecting; may be porous or nonporous; etc. A solid support as described above can be formed of any suitable material, including metals, metal oxides, semiconductors, polymers (particularly organic polymers in any suitable form including woven, nonwoven, molded, extruded, cast, etc.), silicon, silicon oxide, and composites thereof.

Suitable materials for use as substrates include, but are not limited to, polycarbonate, gold, silicon, silicon oxide, silicon oxynitride, indium, tantalum oxide, niobium oxide, titanium, titanium oxide, platinum, iridium, indium tin oxide, diamond or diamond-like film, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polyacrylonitrile (PAN), polyacrylate, polycarbonate, polybutylene terephthalate (PBT), poly(ethylene) (PE) (including low density, linear low density, high density, cross-linked and ultra-high molecular weight grades), poly(propylene) (PP), cis and trans isomers of poly(butadiene) (PB), cis and trans isomers of poly(isoprene), polyethylene terephthalate) (PET), polypropylene homopolymer, polypropylene copolymers, polystyrene (PS) (including general purpose and high impact grades), polycarbonate (PC), poly(epsilon-caprolactone) (PECL or PCL), poly(methyl methacrylate) (PMMA) and its homologs, poly(methyl acrylate) and its homologs, poly (lactic acid) (PLA), poly(glycolic acid), polyorthoesters, poly(anhydrides), nylon, polyimides, polydimethylsiloxane (PDMS), polybutadiene (PB), polyvinylalcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), styrene maleic anhydride (SMA), metal oxides, glass, silicon oxide or other inorganic or semiconductor material (e.g., silicon nitride), compound semiconductors (e.g., gallium arsenide, and indium gallium arsenide), and combinations thereof.

Examples of well-known solid supports include polypropylene, polystyrene, polyethylene, dextran, nylon, amylases, glass, natural and modified celluloses (e.g., nitrocellulose), polyacrylamides, agaroses and magnetite. In some instances, the solid support can be silica or glass because of its great chemical resistance against solvents, its mechanical stability, its low intrinsic fluorescence properties, and its flexibility of being readily functionalized. In one embodiment, the substrate can be glass, particularly glass coated with nitrocellulose, more particularly a nitrocellulose-coated slide (e.g., FAST slides).

In some embodiments, the support can be planar. In some instances, the support can be spherical. In some instances, the support can be a bead. In some instances, a support can be magnetic. In some instances, a magnetic solid support can comprise magnetite, maghemitite, FePt, SrFe, iron, cobalt, nickel, chromium dioxide, ferrites, or mixtures thereof. In some instances, a support can be nonmagnetic. In some embodiments, the nonmagnetic solid support can comprise a polymer, metal, glass, alloy, mineral, or mixture thereof. In some instances a nonmagnetic material can be a coating around a magnetic solid support. In some instances, a magnetic material may be distributed in the continuous phase of a magnetic material. In some embodiments, the solid support comprises magnetic and nonmagnetic materials. In some instances, a solid support can comprise a combination of a magnetic material and a nonmagnetic material. In some embodiments, the magnetic material is at least about 5, 10, 20, 30, 40, 50, 60, 70, or about 80% by weight of the total composition of the solid support. In some embodiments, the bead size can be quite large, on the order of 100-900 microns or in some cases even up to a diameter of 3 mm. In other embodiments, the bead size can be on the order of 1-150 microns. The average particle diameters of beads can be in the range of about 2 μm to several millimeters, e.g., diameters in ranges having lower limits of 2 μm, 4 μm, 6 μm, 8 μm, 10 μm, 20 μm, 30 μm, 40 μm, 50 μm, 60 μm, 70 μm, 80 μm, 90 μm, 100 μm, 150 μm, 200 μm, 300 μm, or 500 μm, and upper limits of 20 μm, 30 μm, 40 μm, 50 μm, 60 μm, 70 μm, 80 μm, 90 μm, 100 μm, 150 μm, 200 μm, 300 μm, 500 μm, 750 μm, 1 mm, 2 mm, or 3 mm.

In some embodiments, the support can comprise an array. In some embodiments, the array comprises a target analyte. In some embodiments, the target analyte comprises a nucleoside, a nucleotide, a polynucleotide, a peptide, a peptoid, a saccharide, a polysaccharide, an aptamer, or an antibody or fragment thereof. In some embodiments, the target analyte comprises a library of target analytes.

In some embodiments, an array comprises a library of molecules. In some embodiments, the array can comprise at least about 100, 1000, 10,000, 100,000, $10^6$, $10^7$, $10^8$, $10^9$, $10^{10}$, $10^{11}$, $10^{12}$, $10^{13}$, or $10^{14}$, $10^{15}$ molecules per 1 cm$^2$. In some embodiments, a molecule can comprise a sequence of monomers. In some embodiments, the sequence of monomers can comprise a sequence of amino acids. In some embodiments, a feature can be a region on a substrate from about 0.5 microns to about 200 microns in diameter. In some embodiments, the array can have a plurality of features. In some embodiments, the center-to-center distance between features can be from about 1 micron to about 300 microns. In some embodiments, the array can comprise at least about 1,000, 10,000, 100,000, 200,000, 300,000, 400,000, 500,000, 600,000, 700,000, 800,000, 900,000, 1 million, 1.5 million, 2 million, 2.5 million, 3 million, 3.5 million, or 4 million features per 1 cm$^2$. In some embodiments, at least about 40% of the molecules in the library are distinct. In some embodiments, at least about 50% of the molecules in the library are distinct. In some embodiments, at least about 60% of the molecules in the library are distinct. In some embodiments, at least about 70% of the molecules in the library are distinct. In some embodiments, at least about 80% of the molecules in the library are distinct. In some embodiments, at least about 90% of the molecules in the library are distinct. In some embodiments, at least 50% of the molecules in the library are at least 3, 4, 5, 6, 7, 8, 9, 10, 11, 12, 13, 14, 15, 16, 17, 18, 19, 20, 30, 40, 50, 60, 70, 80, 90, or 100 monomers in length. In some embodiments, at least 50% of the molecules in the library are at most 3, 4, 5, 6, 7, 8, 9, 10, 11, 12, 13, 14, 15, 16, 17, 18, 19, 20, 30, 40, 50, 60, 70, 80, 90, or 100 monomers in length. In some embodiments, the library comprises a median monomer length of about 3, 4, 5, 6, 7, 8, 9, 10, 11, 12, 13, 14, 15, 16, 17, 18, 19, 20, 30, 40, 50, 60, 70, 80, 90, or 100 monomers. In some embodiments, the array can comprise at least 10,000, 50,000, 100,000, 200,000, 300,000, 400,000, 500,000, 600,000, 700,000, 800,000, 900,000, $10^6$, or $10^7$ sequentially distinct library molecules. In some embodiments, the array substrate can be selected from wafers, slides, and beads. In some embodiments, the library can be an in-situ synthesized chemical library. In some embodiments, the molecules can be polynucleotides, peptides, peptoids, or polysaccharides.

Binding Moiety

An analyte binding moiety, also referred to as a binding moiety (or domain) can be the region, molecule, domain, portion, fragment, or moiety that binds to a target analyte. Thus, a binding moiety confers the ability to bind or specifically bind to given target. A binding moiety can be a nucleic acid molecule or can be proteinaceous. Binding moieties include, but are not limited to, RNAs DNAs, RNA-DNA hybrids, small molecules (e.g., drugs or metabolites), aptamers, polypeptides, proteins, antibodies, viruses, virus particles, cells, fragments thereof, and combinations thereof.

In some embodiments, a binding moiety can be a polypeptide, a protein, or any fragment thereof. In some embodiments, a polypeptide or protein can be an engineered or recombinant polypeptide or protein. In some embodiments, a binding moiety is an antibody or fragment thereof. An antibody can be of any isotype (e.g., IgG, IgE, IgM, IgD, IgA and IgY), class ($IgG_1$, $IgG_2$, $IgG_3$, $IgG_4$, $IgA_1$, $IgA_2$), subclass or modified version thereof. Antibodies may include complete immunoglobulins or fragments thereof. An antibody fragment can refer to one or more fragments of an antibody that retains the ability to specifically bind to a target molecule, such as an antigen.

In some embodiments, a binding moiety can be an aptamer. An aptamer is an isolated nucleic acid molecule that binds with high specificity and affinity to a target analyte, such as a protein. An aptamer comprises a three dimensional structure held in certain conformation(s) that provide chemical contacts to specifically bind a given target. In some embodiments, a binding moiety is small molecule. For example, a small molecule can be a macrocyclic molecule, an inhibitor, a drug, or chemical compound. In some embodiments, a binding moiety is a cell. For example, a binding moiety can be an intact cell, a cell treated with a compound (e.g. a drug), a fixed cell, a lysed cell, or any combination thereof.

Detection Methods

Detection methods for detecting bound binding moieties can include photometric and non-photometric means. In some embodiments, such methods process includes a method to detect and measure absorbance, fluorescence, refractive index, polarization or light scattering. These include direct and/or indirect means to measure such parameters. Methods involving fluorescence include fluorescent tagging in immunological methods such as ELISA or sandwich assay. Methods involving refractive index include surface Plasmon resonance (SPR), grating coupled methods (e.g. sensors uniform grating couplers, wavelength-interrogated optical sensors (WIOS) and chirped grating couplers), resonant minor and interferometric techniques. Methods involving polarization include ellipsometry. Light scattering methods may also be used. Other means for tagging and/or separating and/or detecting can also include magnetic means. Magnetic resonance imaging (MRI), or gas phase ion spectrometry, may all be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules. Gas phase ion spectrometers include mass spectrometers, ion mobility spectrometers and total ion current measuring devices.

Binding assays can also be useful, e.g., for identifying disease related antibodies (binding moieties) that interact with the target analytes described herein. For example, antibodies or other molecules that bind target anlaytes can be identified in binding assays. Binding assays can involve, but are not limited to, use of isolated polypeptides, crude extracts, or cell-based assays. In some embodiments the assays described herein can be used to a) identify subjects whose have a first disease or a second disease; (b) assess the impact of an disease therapy; and (c) monitor disease progression.

Binding assays can involve contacting a target analyte with a sample comprising a binding moiety (antibody) and allowing sufficient time for the molecule and test agents to form a binding complex. Any binding complexes formed can be detected using any of a number of established analytical techniques. Binding assays include, but are not limited to, methods that measure co-precipitation or co-migration on non-denaturing SDS-polyacrylamide gels, co-migration on Western blots, enzyme linked immunosorbent assay (ELISA), radioimmunoassay (RIA), immunoradiometric assay, fluoroimmunoassay, chemiluminescent assay, bioluminescent assay, fluorescence activated cell sorting (FACS), or fluorescence resonance energy transfer (FRET).

Diagnostics

The methods and apparatus disclosed herein can be used to screen for various diseases or conditions, including an alteration in the state of the body or of some of the organs, interrupting or disturbing the performance of the functions and/or causing symptoms such as discomfort, dysfunction, distress, or even death to the person afflicted or those in contact with the person. A disease or condition can also include a distemper, ailment, malady, disorder, sickness, illness, complain, interdisposition and/or affectation.

For example, samples containing binding moieties from a diseased animal can be simultaneously screened for the binding moieties' ability to interact with an array. These interactions can be compared to those of samples from individuals that are not in a disease state, not presenting symptoms of persons in the disease state, or presenting symptoms of the disease state. For example, the levels of binding moieties in samples from a diseased animal can be simultaneously determined. These levels can be compared to those of samples from individuals that are not in a disease state, not presenting symptoms of persons in the disease state, or presenting symptoms of the disease state.

The methods, kits, and compositions described herein can be used in medical diagnostics, drug discovery, molecular biology, immunology and toxicology. Arrays can be used for large scale binding assays in numerous diagnostic and screening applications. The multiplexed measurement of quantitative variation in levels of large numbers of target analytes (e.g. proteins) allows the recognition of patterns defined by several to many different target analytes. The multiplexed identification of large numbers of interactions between target analytes and binding moieties allows for the recognition of binding and interaction patterns defined by several to many different interactions between target analytes and binding moieties. Many physiological parameters and disease-specific patterns can be simultaneously assessed. One embodiment involves the separation, identification and characterization of proteins present in a biological sample. For example, by comparison of disease and control samples, it is possible to identify disease specific target analytes. These target analytes can be used as targets for drug development or as molecular markers of disease.

In some embodiments, methods can be methods for diagnosing or detecting a disease or condition such as a cancer, inflammatory disease, immune disease, autoimmune disease, cardiovascular disease, neurological disease, infectious disease, metabolic disease, or a perinatal condition. For example, the disease or condition can be a tumor, neoplasm, or cancer. The cancer can be, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, or Burkitt's lymphoma. The disease or condition can also be a premalignant condition, such as Barrett's Esophagus. The disease or condition can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The disease or condition can also be a cardiovascular disease, such as atherosclerosis, congestive heart failure, vulnerable plaque, stroke, or ischemia. The cardiovascular disease or condition can be high blood pressure, stenosis, vessel occlusion or a thrombotic event. The disease or condition can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neuropsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The condition may also be fibromyalgia, chronic neuropathic pain, or peripheral neuropathic pain. The disease or condition may also be an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. The disease or condition can also be a perinatal or pregnancy related condition (e.g. preeclampsia or preterm birth), zika virus, dengue fevor, flavivirus, or a metabolic disease or condition, such as a metabolic disease or condition associated with iron metabolism.

In some embodiments, methods are methods for diagnosing or detecting an autoimmune disorder. In some embodiments, methods can be methods for determining a disease or condition or the progression of a disease or condition. Non-limiting examples of disorder associated with the immune system can include: autoimmune disorders, inflammatory diseases, HIV, rheumatoid arthritis, diabetes mellitus type 1, systemic lupus erythematosus, scleroderma, multiple sclerosis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis.

Kits

Also provided are kits that find use in practicing the subject methods, as mentioned above. A kit can include one or more of the compositions described herein. A kit can include at least one nucleoside, nucleotide, polynucleotide, peptide, peptoid, saccharide, aptamer, or antibody or fragment thereof. A kit can include at least one binding moiety.

A kit can include a solid support. In some embodiments, the solid support is already functionalized with at least one molecule of structure I. In some embodiments, the solid support is already functionalized with at least one nucleoside, nucleotide, polynucleotide, peptide, peptoid, saccharide, aptamer, or antibody or fragment thereof. A kit can include a reagent for coupling at least one nucleoside, nucleotide, polynucleotide, peptide, peptoid, saccharide, aptamer, or antibody or fragment thereof to the solid support.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, such as printed information on a suitable medium or substrate (e.g., a piece or pieces of paper on which the information is printed), in the packaging of the kit, in a package insert, etc. Yet another means would be a computer readable medium (e.g., diskette, CD, etc.), on which the information has been recorded. Yet another means that may be present is a website address which may be used via the internet to access the information at a removed site.

Communicating a Result

Additional embodiments relate to the communication of assay results or diagnoses or both to technicians, physicians or subjects, for example. In certain embodiments, computers will be used to communicate results of the assessing or diagnoses or both to interested parties, e.g., physicians and their subjects. In some embodiments, the assessing can be performed or results analyzed in a country or jurisdiction which differs from the country or jurisdiction to which the results or diagnoses are communicated. In some embodiments, a diagnosis based on the presence or absence in a test subject of a binding moiety or a binding signature, or signal identified may be communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communication system. In certain embodiments, all or some of the method steps, including the assaying of samples, diagnosing of diseases, and communicating of method results or diagnoses, may be carried out in diverse (e.g., foreign) jurisdictions.

OTHER EMBODIMENTS

The section headings used herein are for organizational purposes only and are not to be construed as limiting the subject matter described.

It is to be understood that the methods and compositions described herein are not limited to the particular methodology, protocols, constructs, and reagents described herein and as such may vary. It is also to be understood that the terminology used herein is for the purpose of describing particular embodiments only, and is not intended to limit the scope of the methods and compositions described herein, which will be limited only by the appended claims. While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the rage is present as if explicitly written out. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed.

EXAMPLES

Example 1—PL8 Linker (HT960-963)

Figure 2:
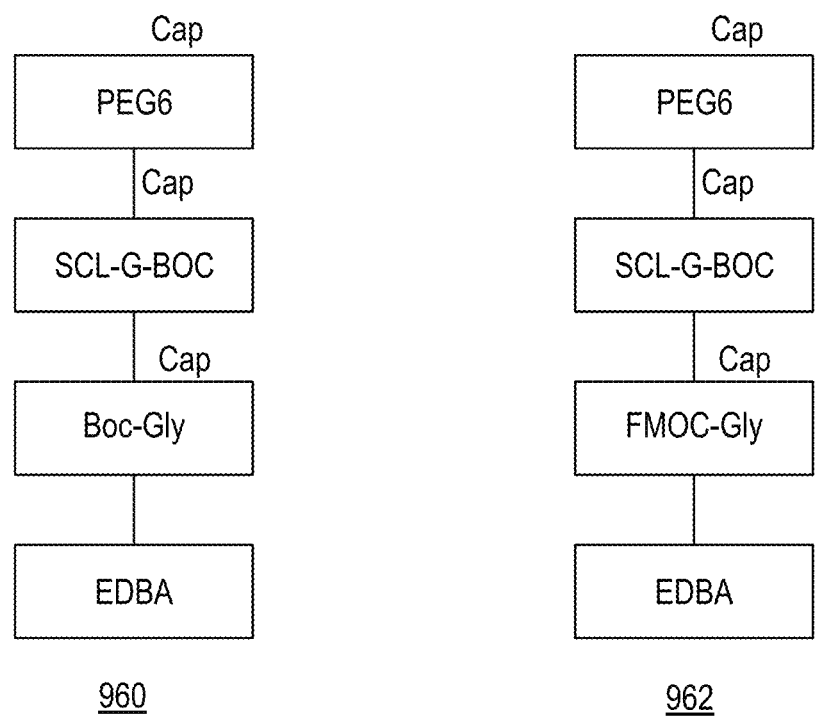
FIG. 2. depicts schematic molecule structures of molecules according to structure I.

FIG. 1 illustrates a molecule (HT960).
FIG. 2 illustrates schematically four molecules (HT960-HT963).

Example 2—Stepwise Coupling of Tetrapeptides to PL8 Linker

The molecule of Example 1 was coupled sequentially to amino acids to form 16 linker-bound tetrapeptides. Vapor phase ammonia cleavage and MALDI analysis were performed after each coupling step to assess the identity and yield for each coupling step.

FIG. 3 shows the results of the coupling sequence for HT960. Average yield after first coupling step was 64%. Average yield after second coupling step was 100%. Average yield after third coupling step was 100%. Average yield after fourth coupling step was 100%.

FIG. 4 shows the results of the coupling sequence for HT962. Average yield after first coupling step was 62%. Average yield after second coupling step was 100%. Average yield after third coupling step was 100%. Average yield after fourth coupling step was 100%.

Example 3 (Prophetic)

Figure 5:
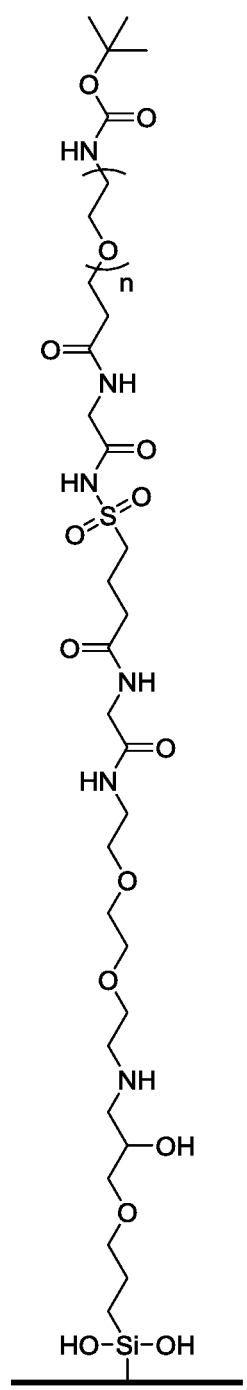
FIG. 5 depicts a molecule. n can be 1-20.

FIG. 5 illustrates a molecule.

Example 4 (Prophetic)

Figure 6:
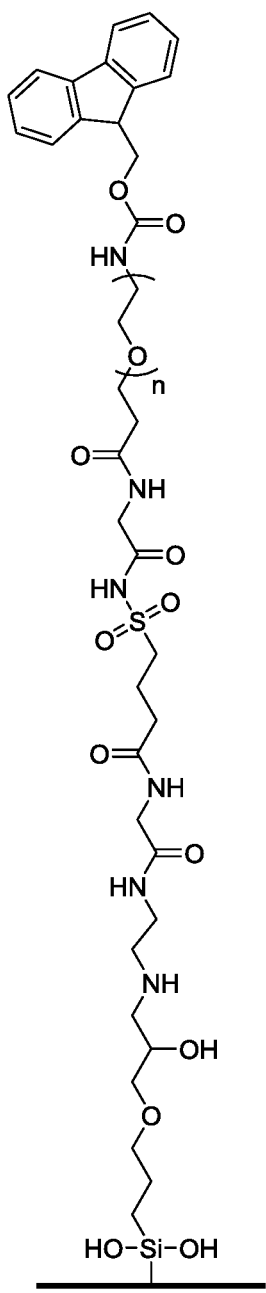
FIG. 6 depicts a molecule. n can be 1-20.

FIG. 6 illustrates a molecule.

Example 5 (Prophetic)

Figure 7:
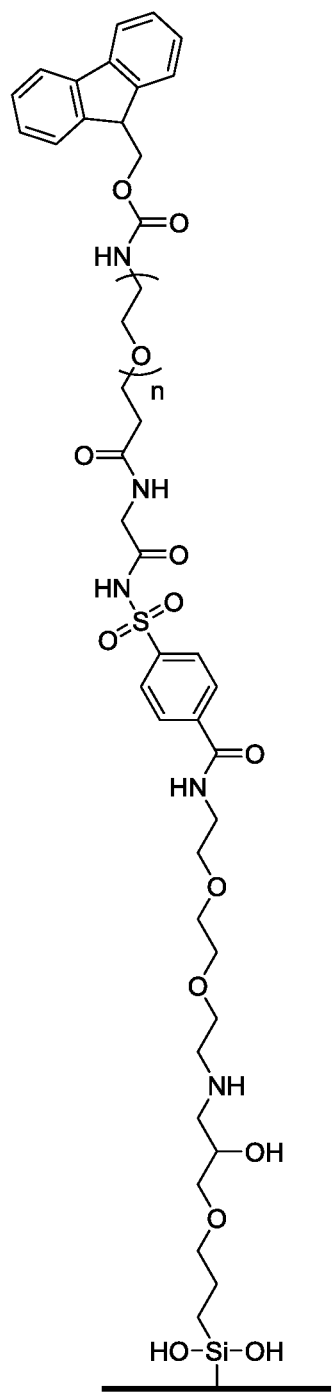
FIG. 7 depicts a molecule. n can be 1-20.

FIG. 7 illustrates a molecule

Example 6 (Prophetic)

Figure 8:
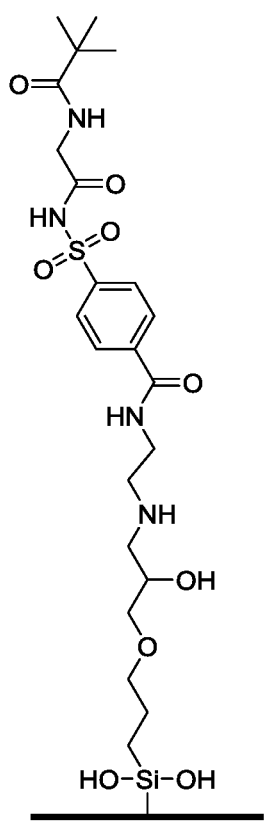
FIG. 8 depicts a molecule.
Figure 9:
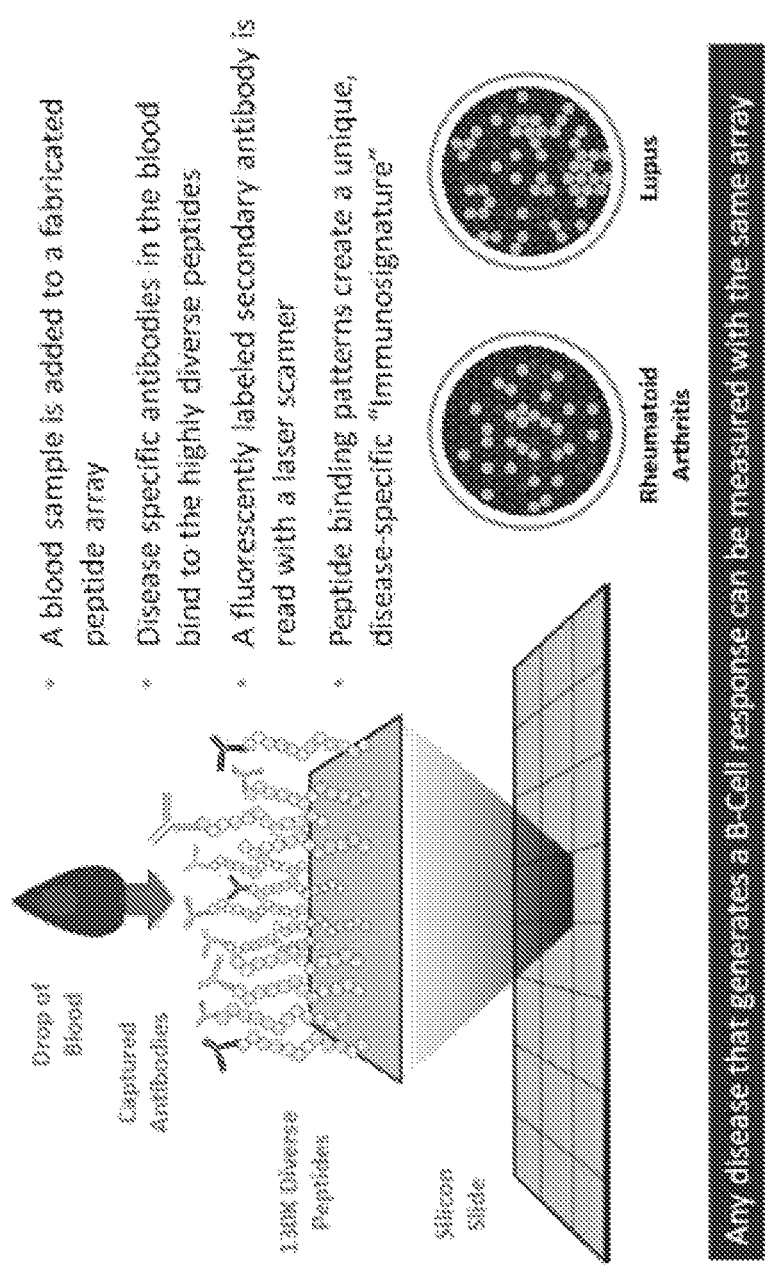
FIG. 9 depicts the use of a molecular array for immunosignaturing.
Figure 10:
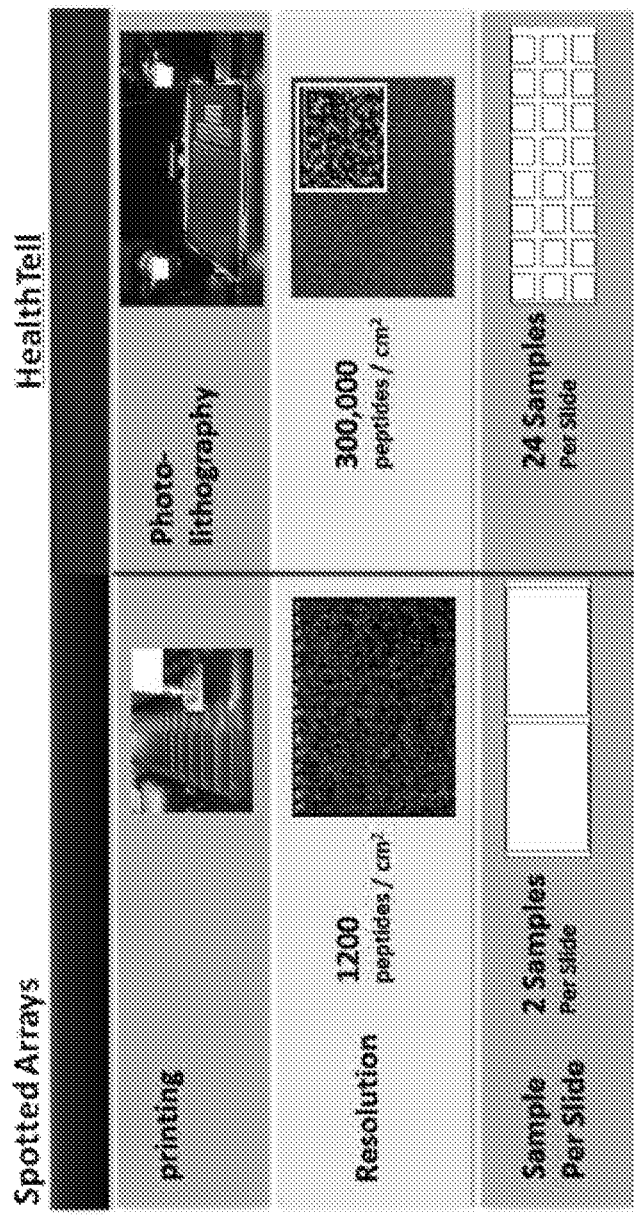
FIG. 10 depicts the arrangement of features on a molecular array.
Figure 12:
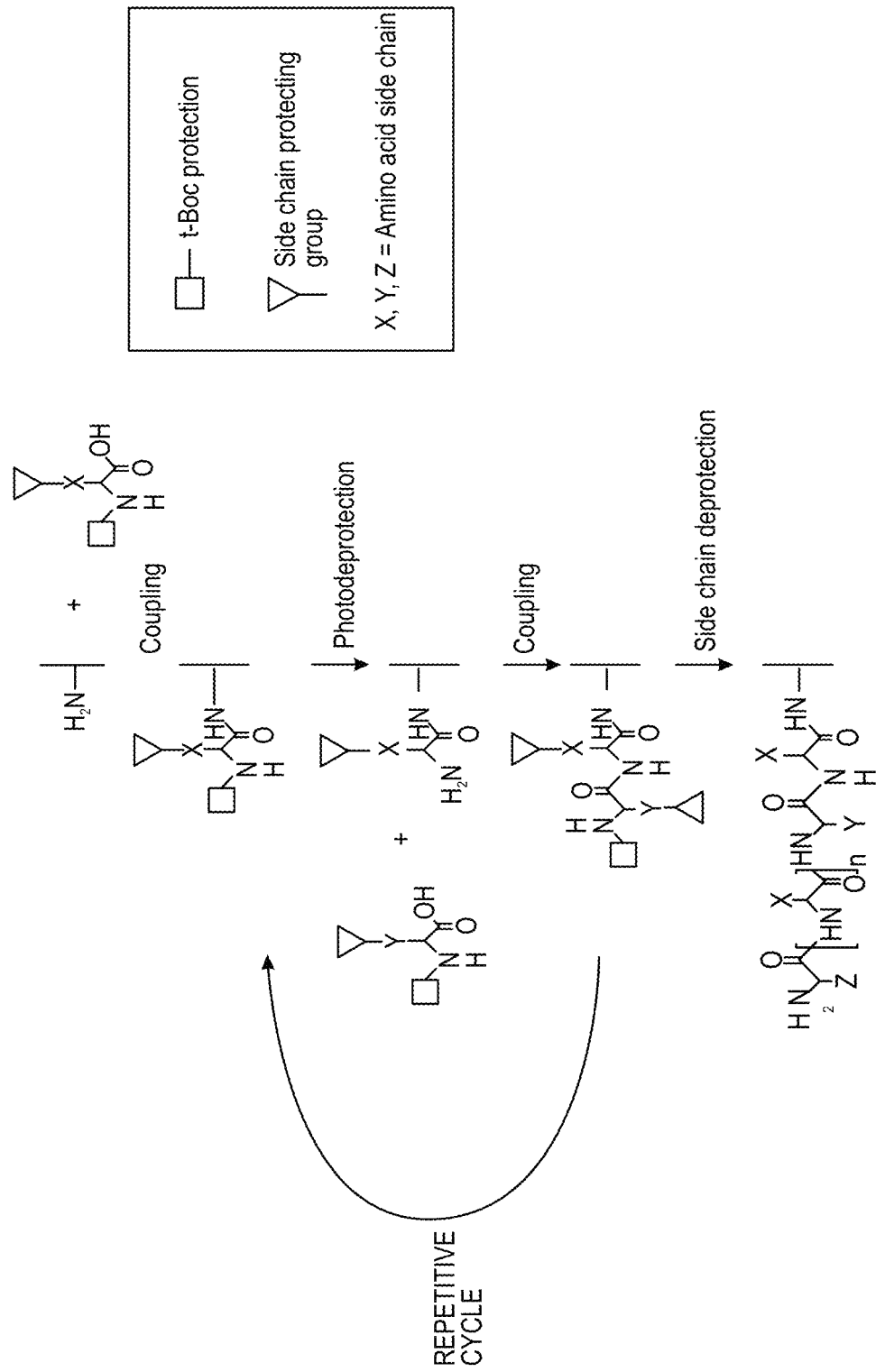
FIG. 12 depicts a scheme for peptide synthesis.
Figure 13:
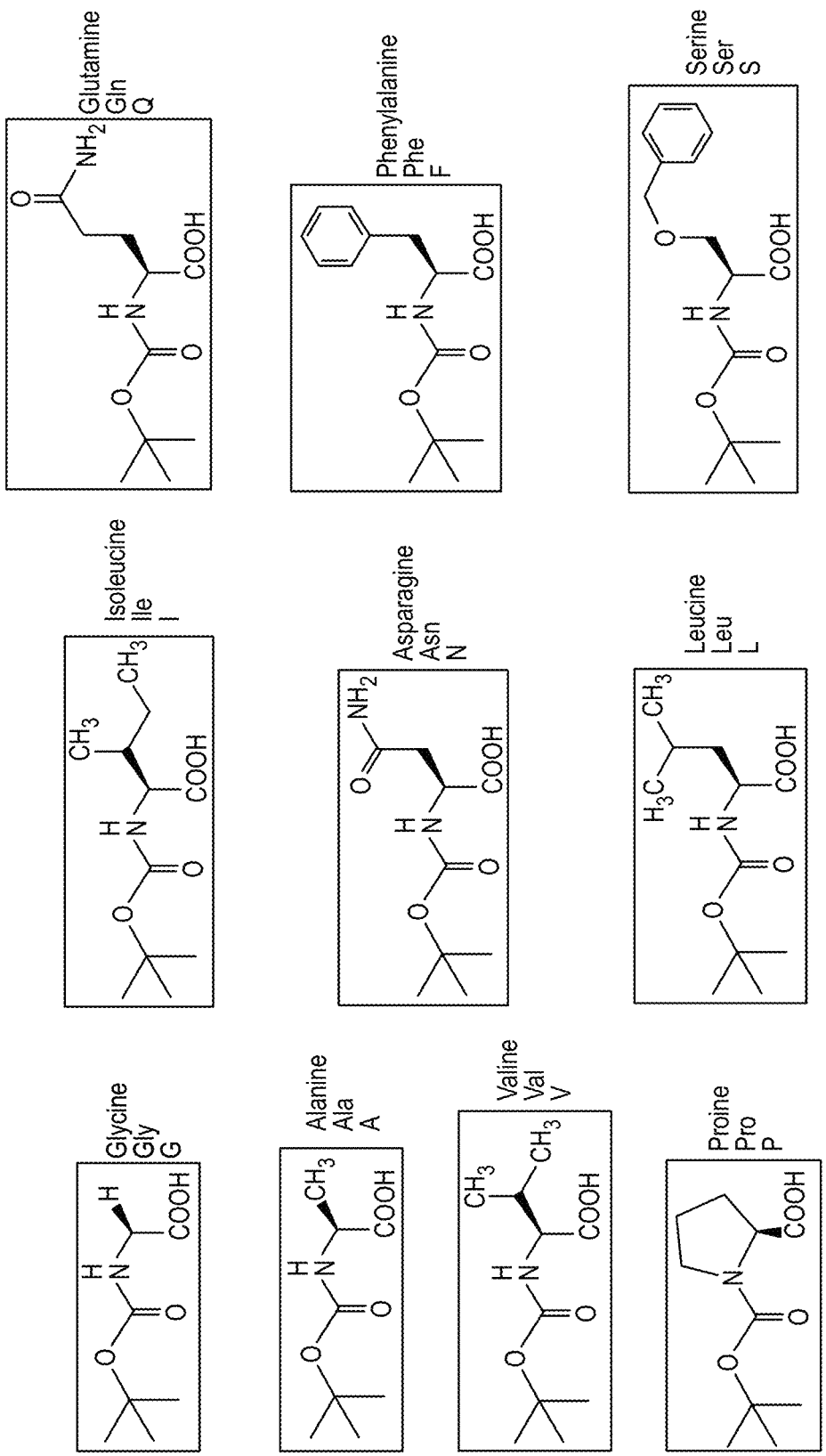
FIG. 13 depicts protected amino acids.
Figure 14:
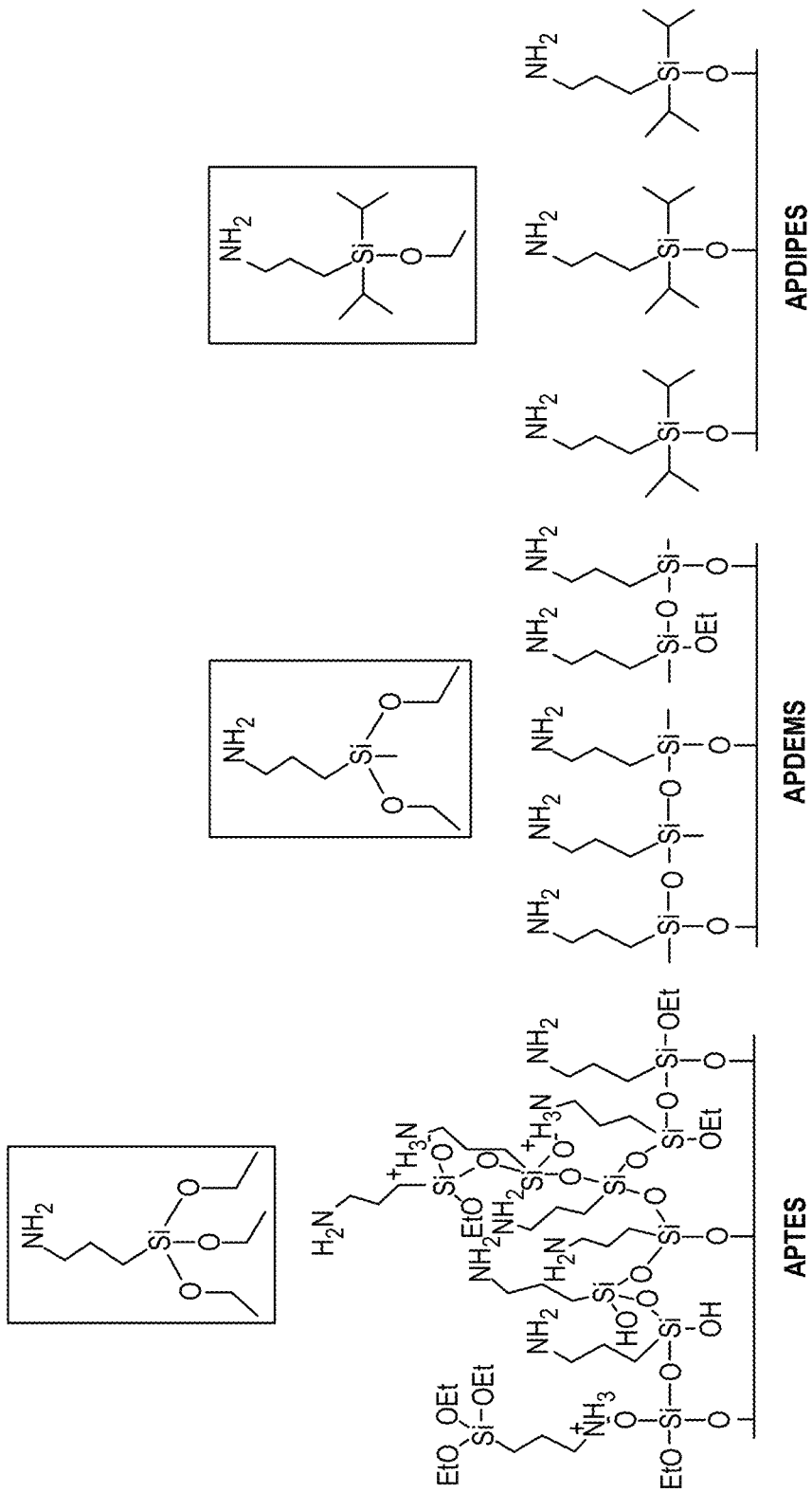
FIG. 14 depicts aminosilane coating structures.
Figure 16:
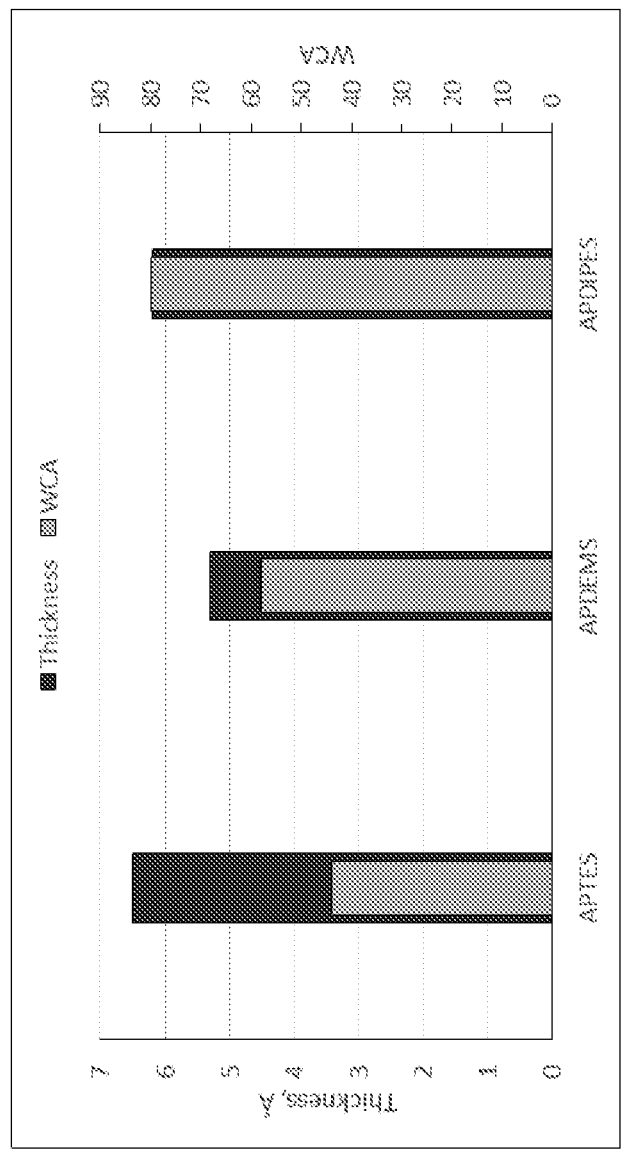
FIG. 16 depicts thickness and water contact angle analysis of amino coatings.
Figure 17:
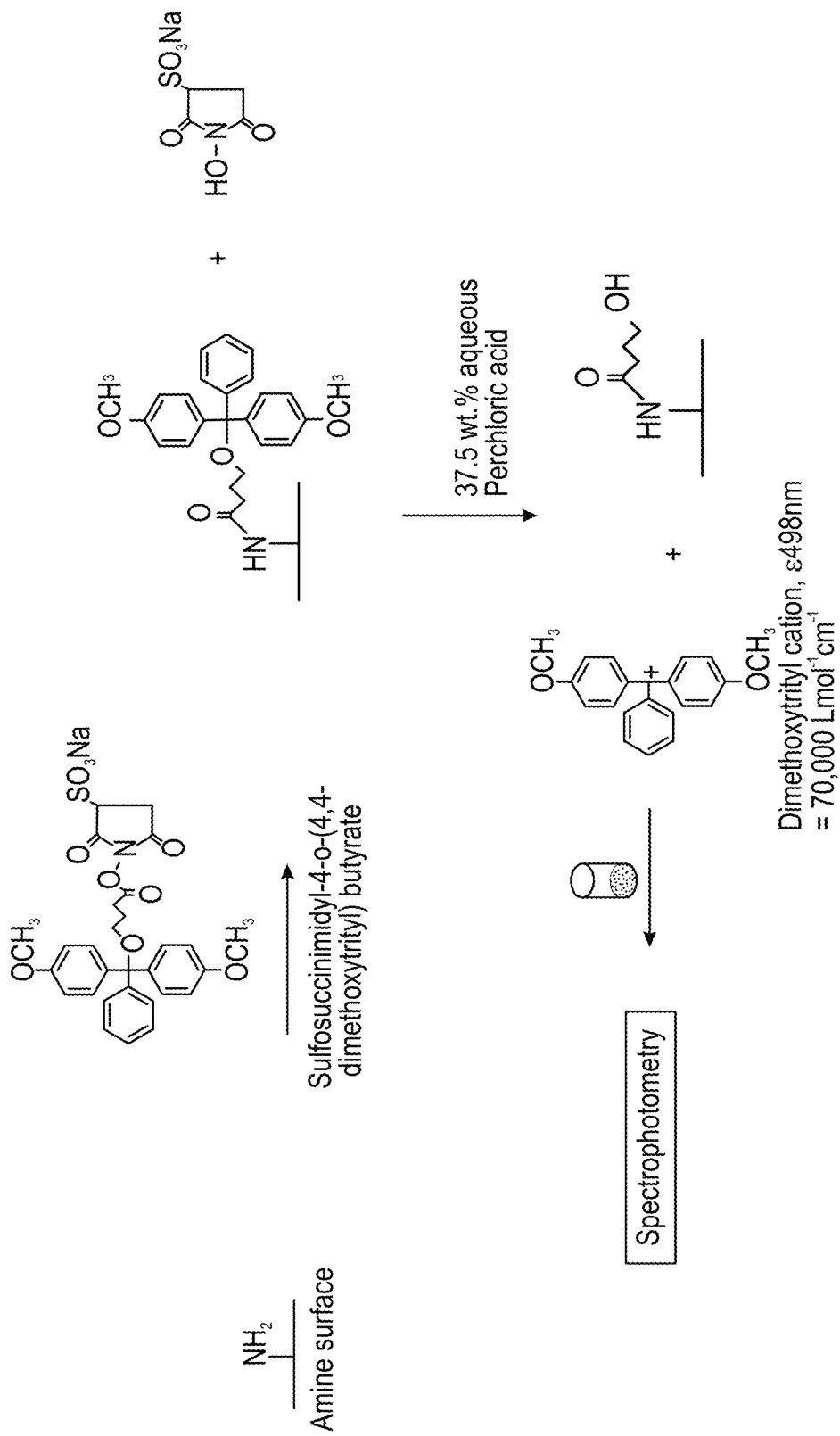
FIG. 17 depicts a scheme for a reactive amine density assay.
Figure 18:
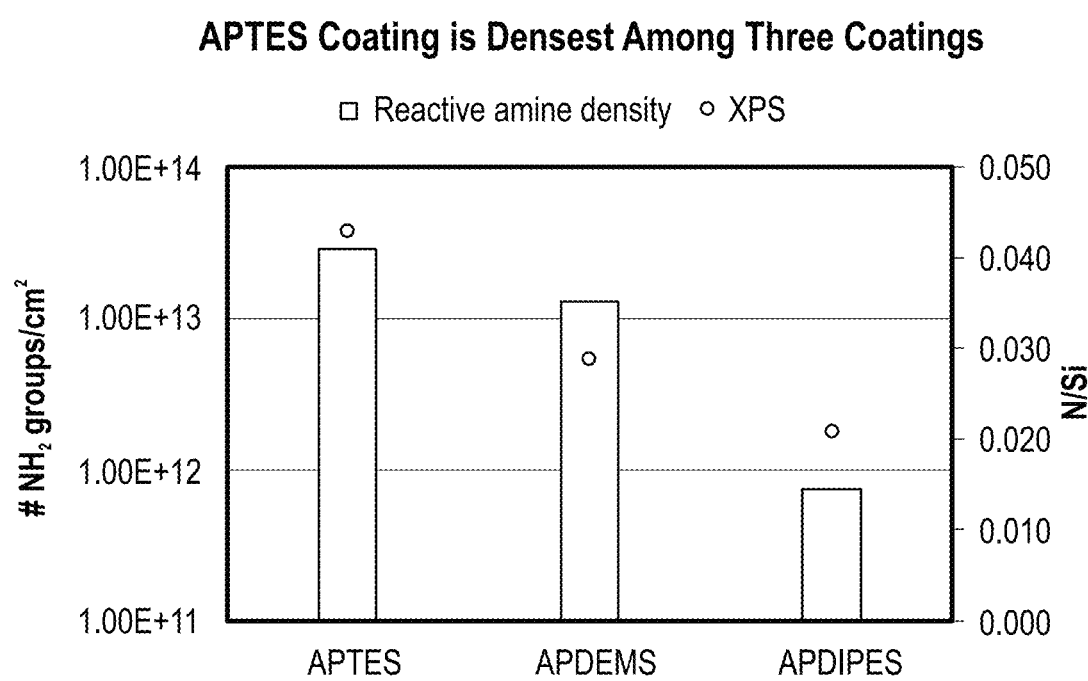
FIG. 18 depicts an amine density analysis of amino coatings.
Figure 19:
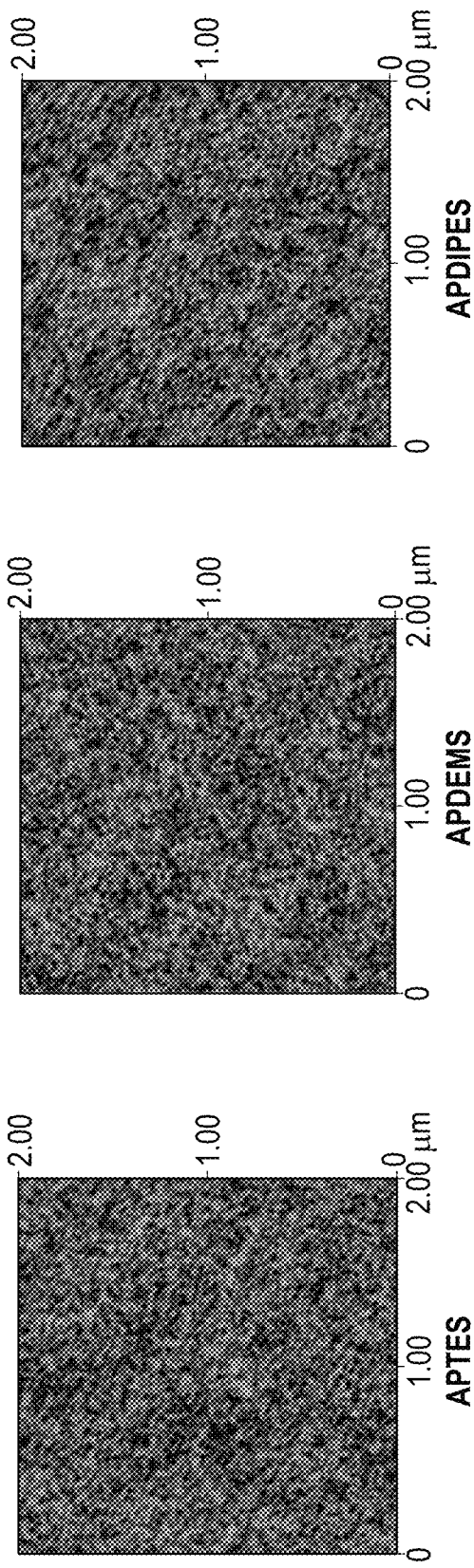
FIG. 19 depicts an AFM analysis of the smoothness of deposition of amino coatings.
Figure 22:
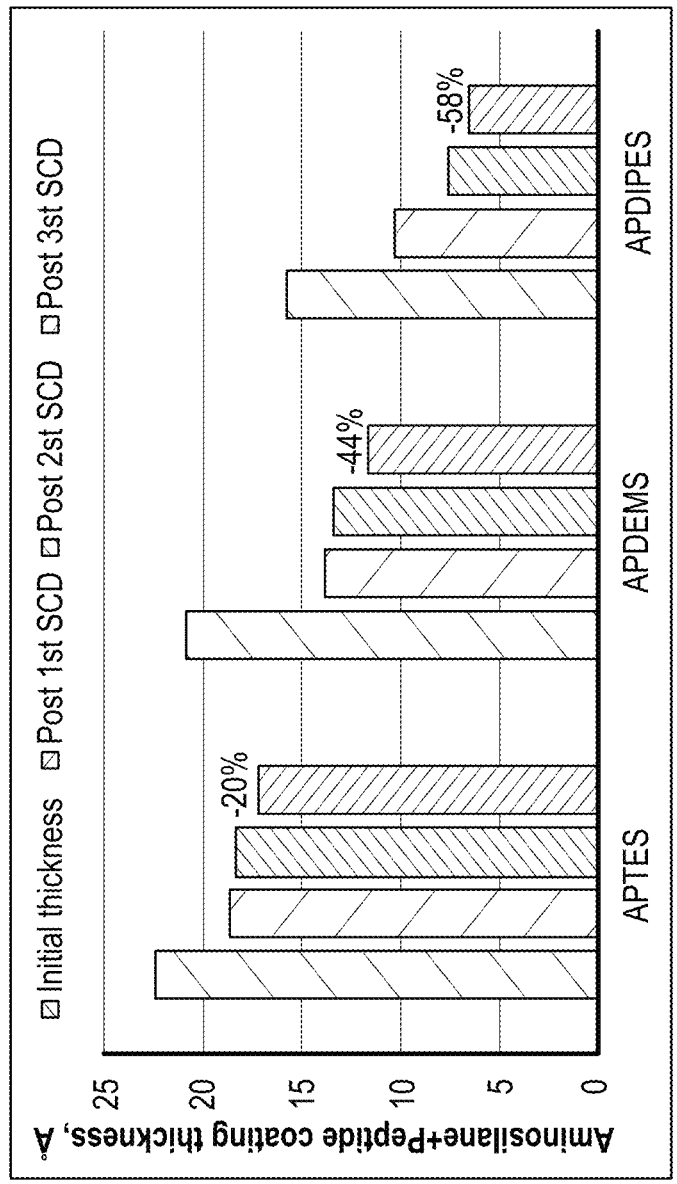
FIG. 22 depicts a thickness analysis of peptide-functionalized amino coatings.
Figure 23:
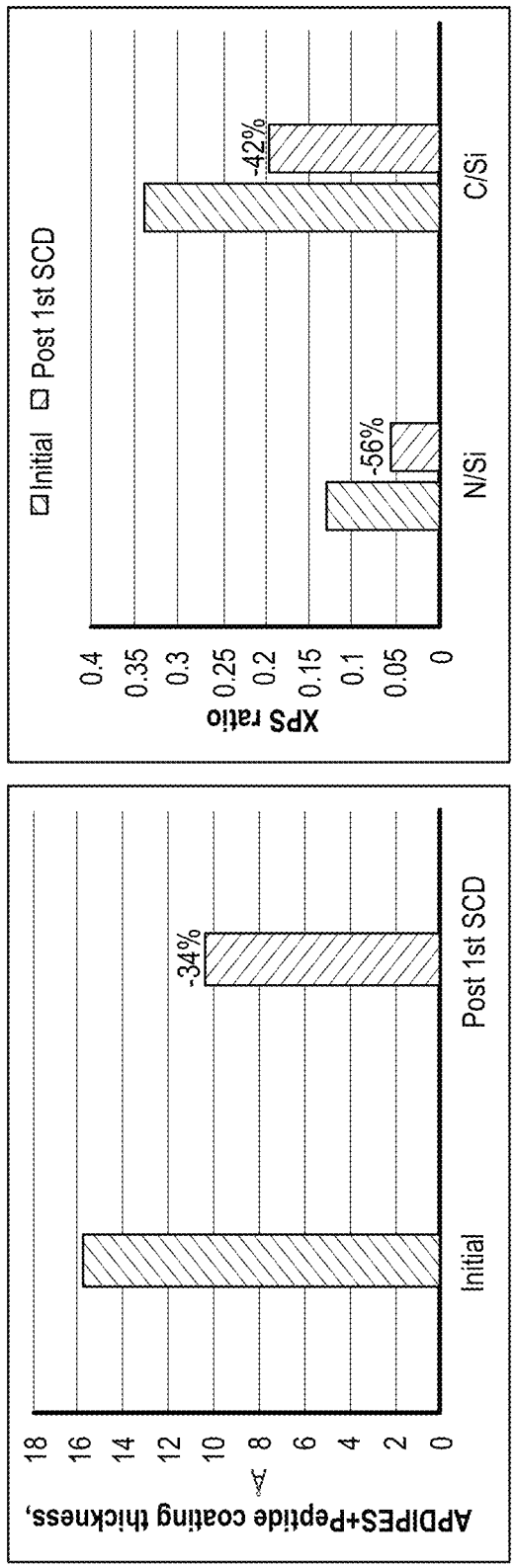
FIG. 23 depicts thickness and XPS analysis of amino coatings.
Figure 24:
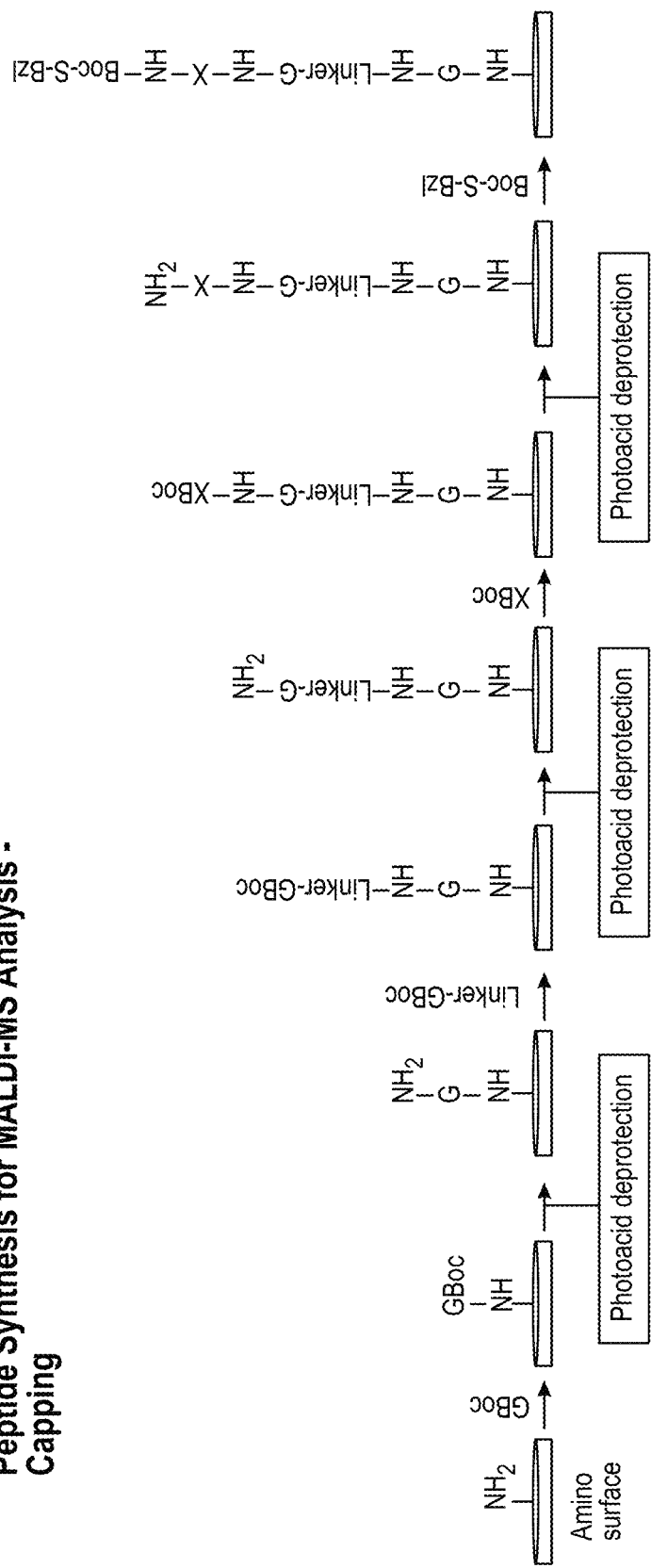
FIG. 24 depicts a scheme for peptide synthesis, amine capping, and MALDI-MS analysis.
Figure 25:
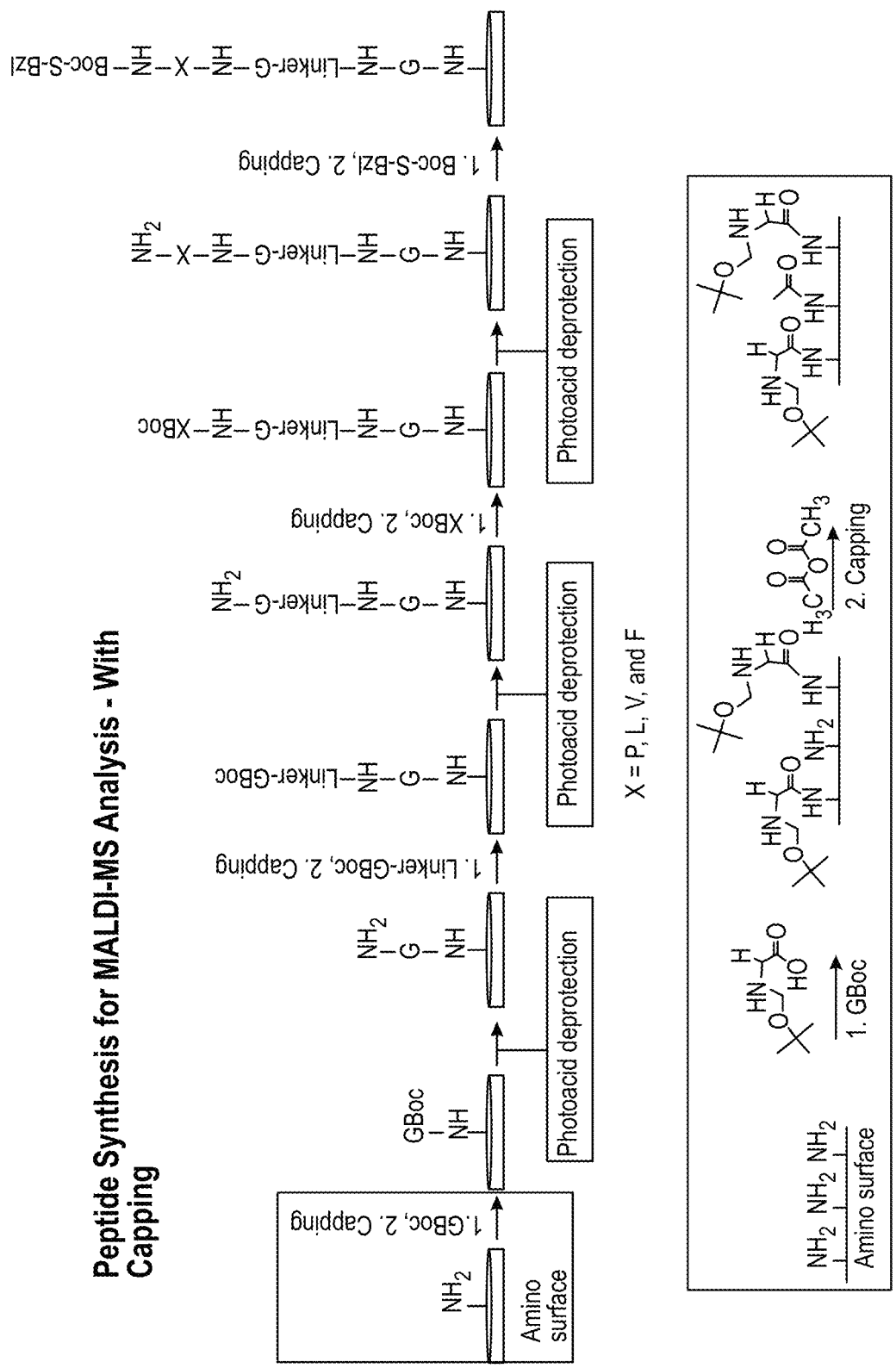
FIG. 25 depicts a scheme for peptide synthesis, amine capping, and MALDI-MS analysis.
Figure 26:
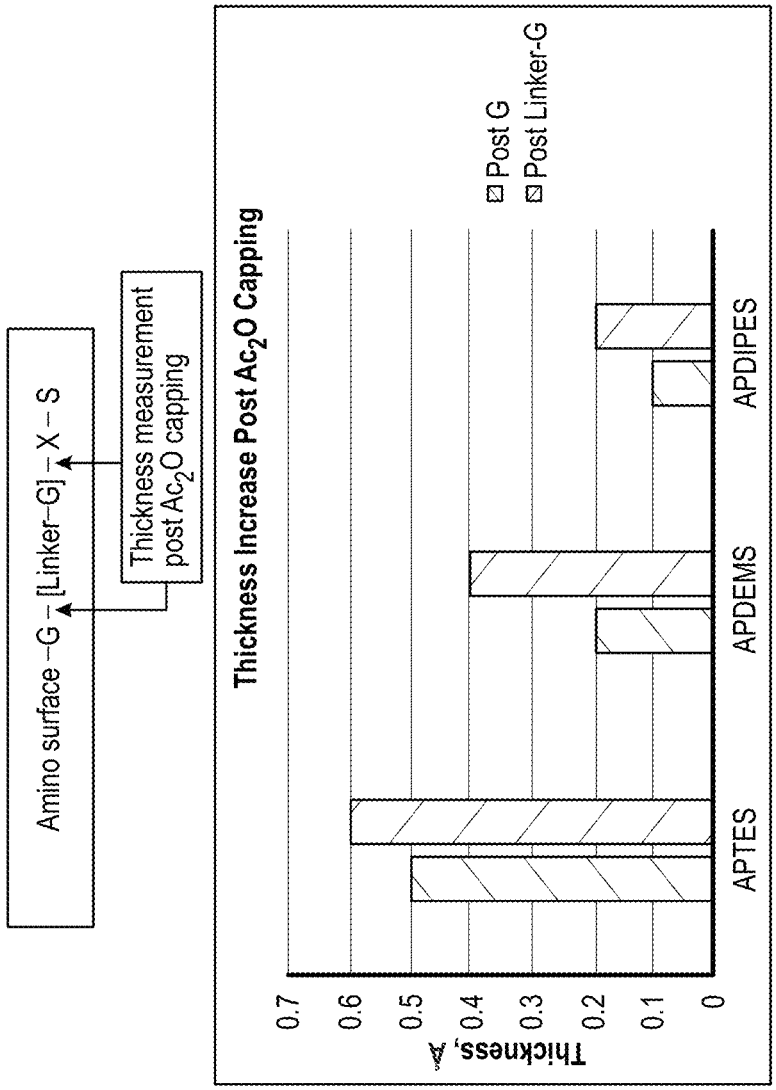
FIG. 26 depicts a thickness analysis of amino coatings.
Figure 27:
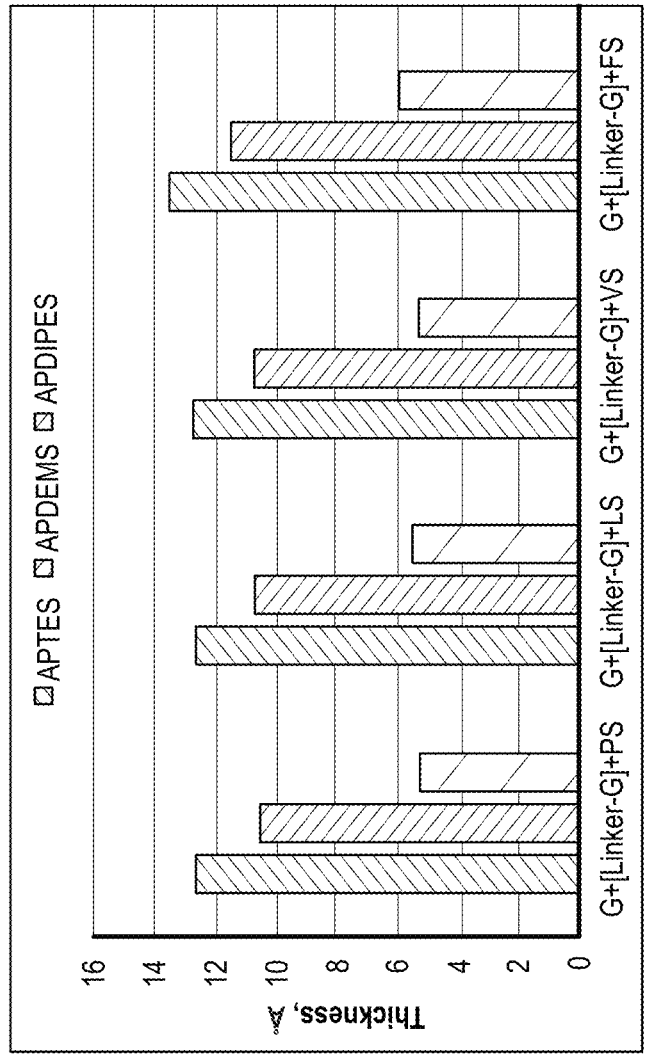
FIG. 27 depicts a thickness analysis of amino coatings.
Figure 28:
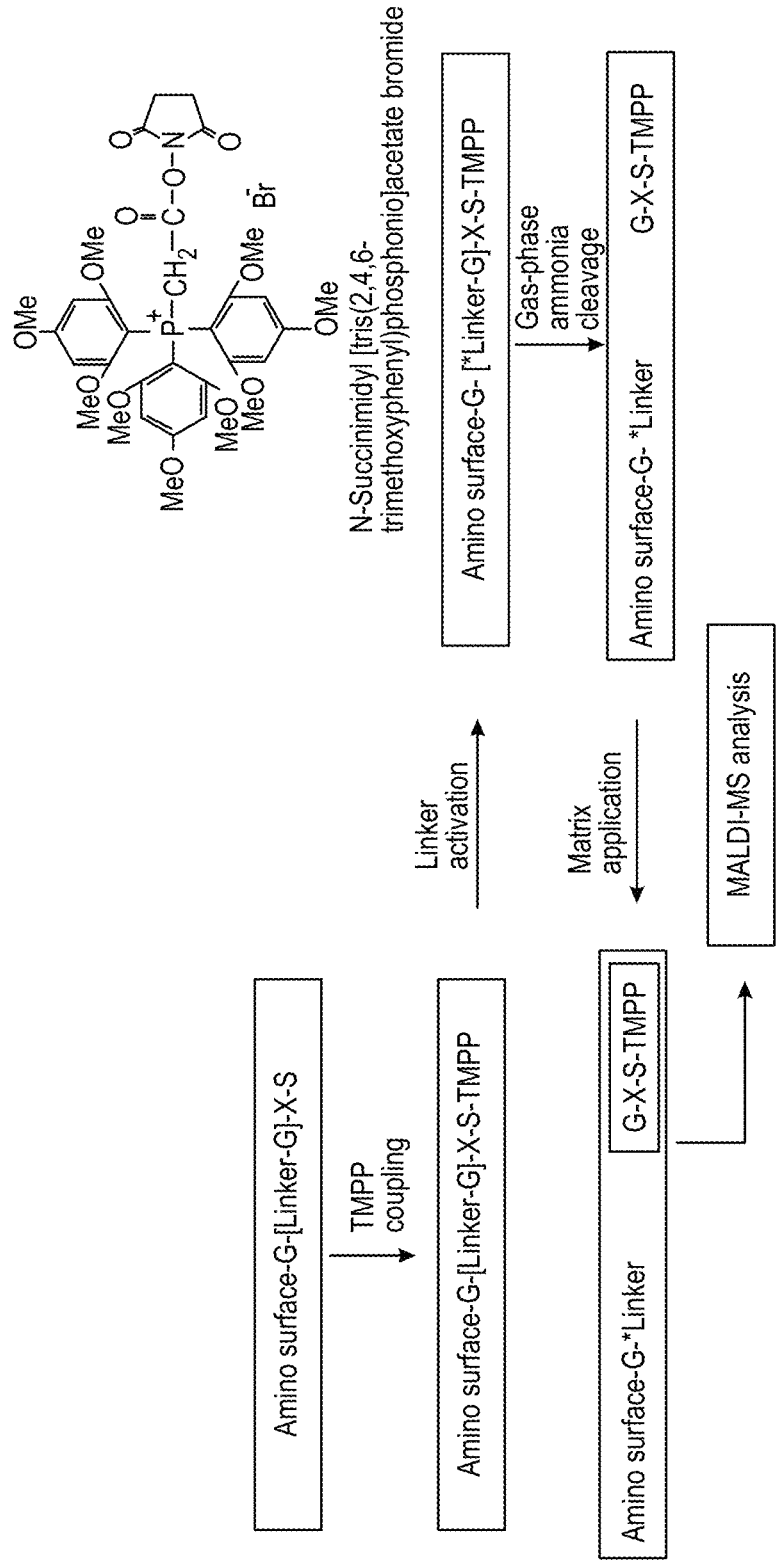
FIG. 28 depicts procedures for surface preparation for MALDI-MS analysis.
Figure 30:
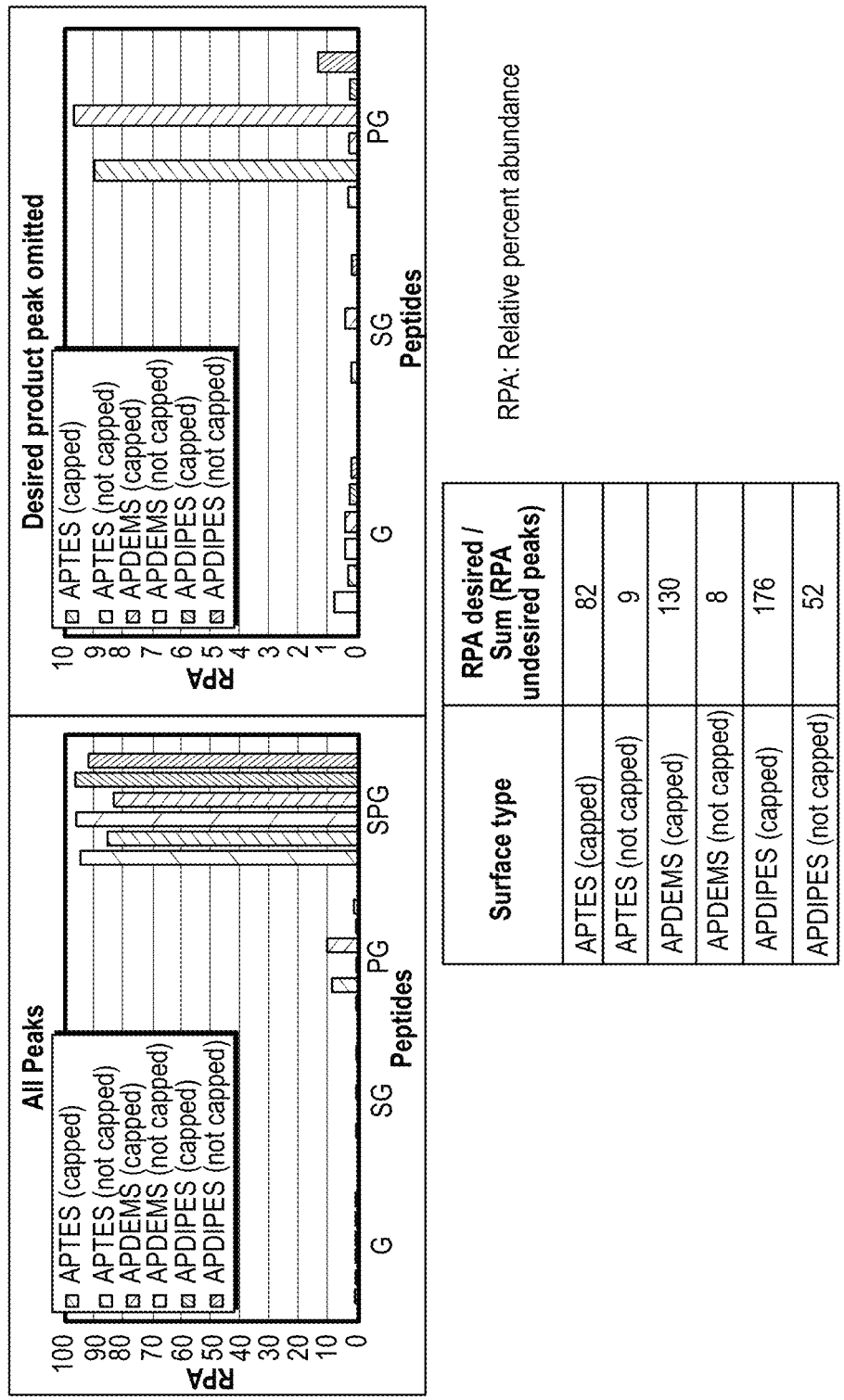
FIG. 30 depicts a purity analysis of peptides synthesized on amino coatings.
Figure 32:
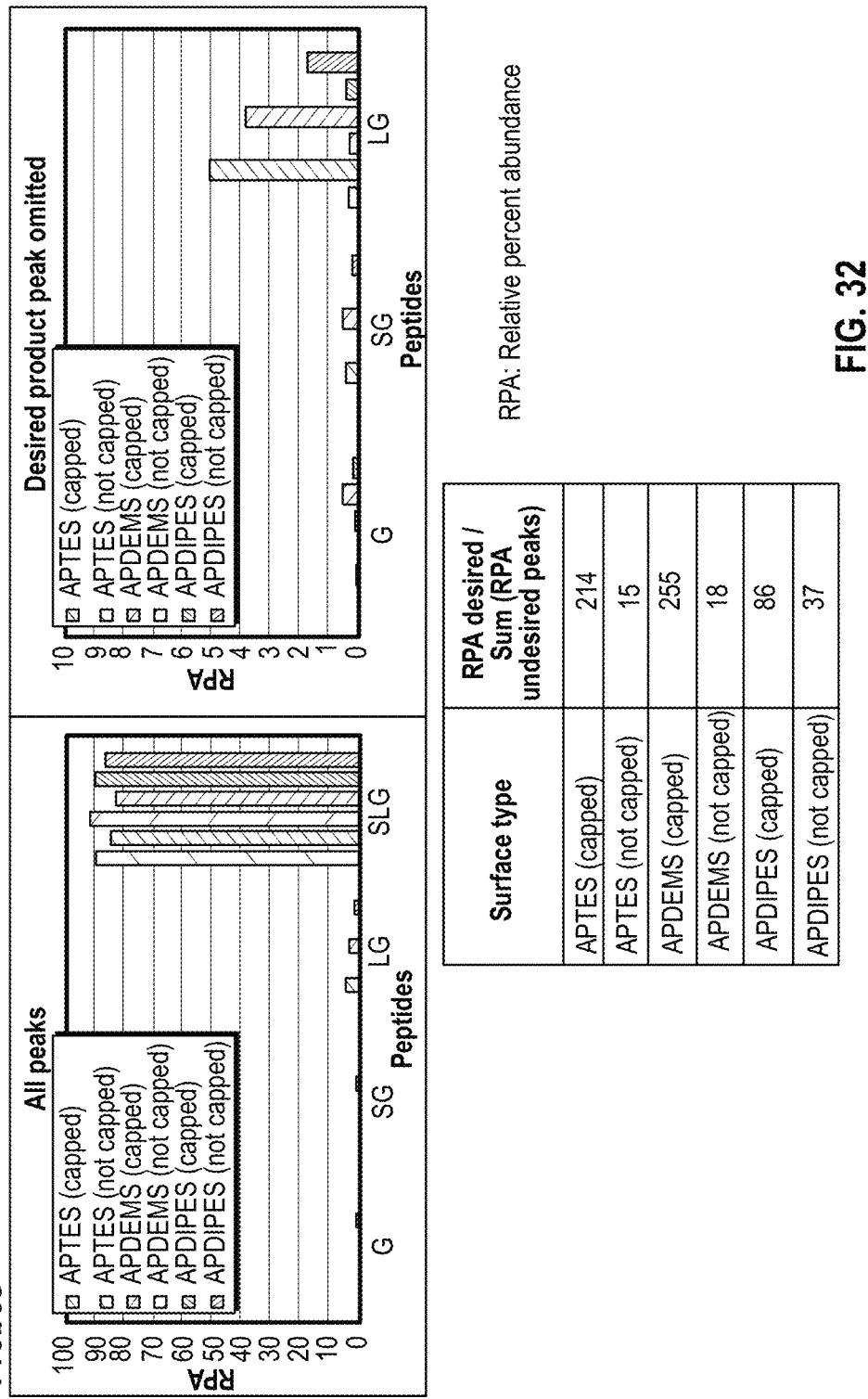
FIG. 32 depicts a purity analysis of peptides synthesized on amino coatings.
Figure 34:
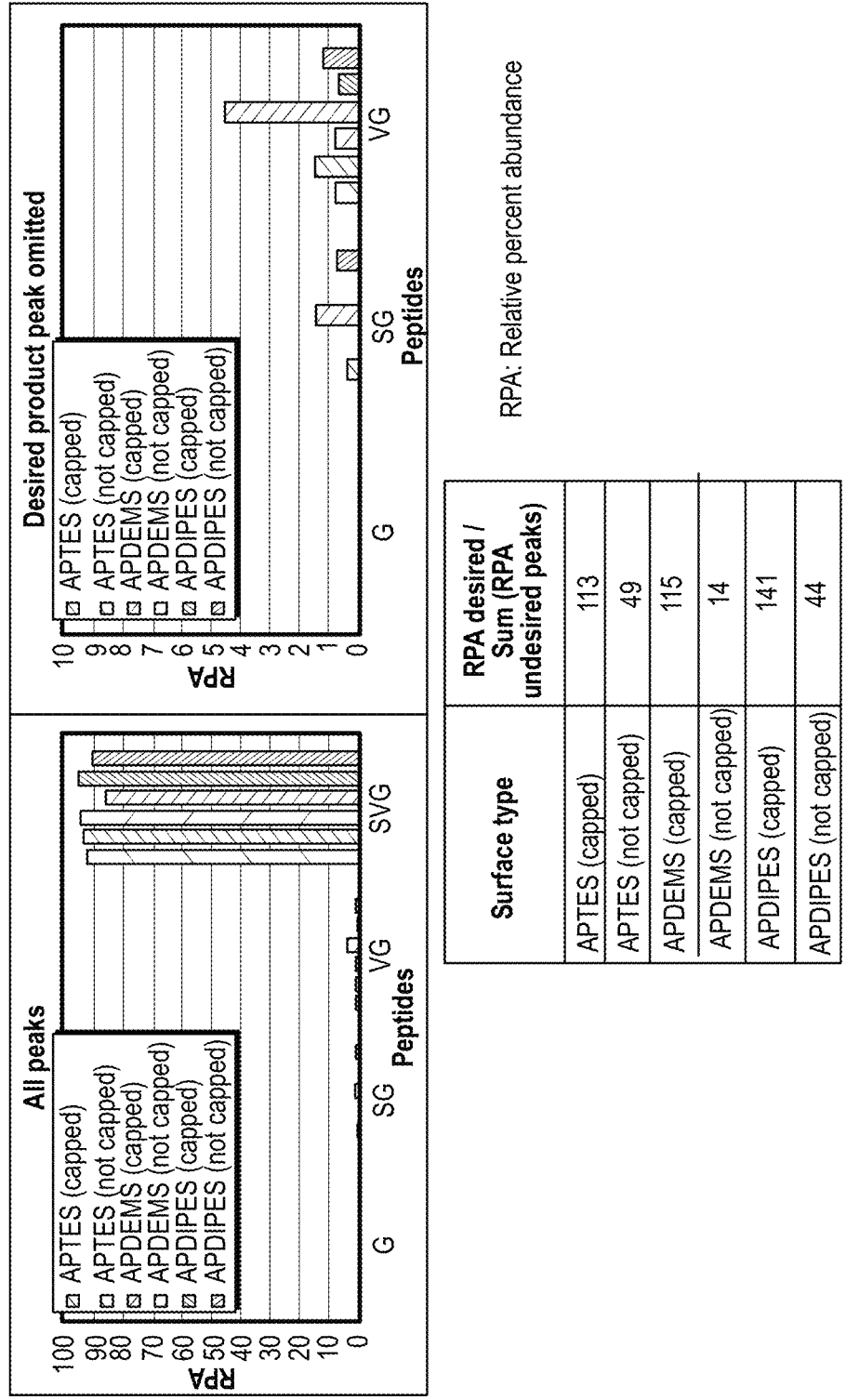
FIG. 34 depicts a purity analysis of peptides synthesized on amino coatings.
Figure 36:
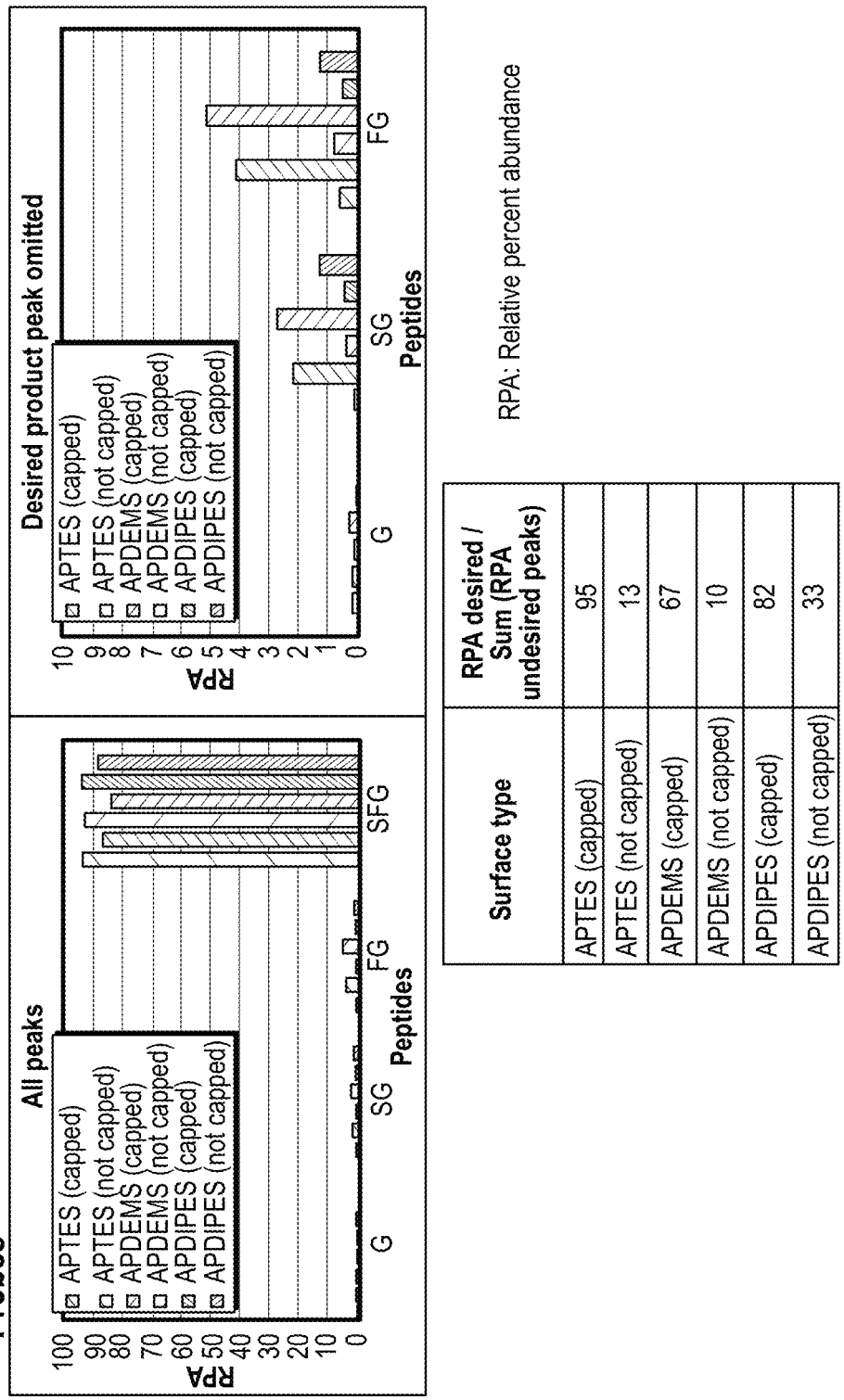
FIG. 36 depicts a purity analysis of peptides synthesized on amino coatings.

FIG. 8 illustrates a molecule

What is claimed is:

1. A molecule having the structure:

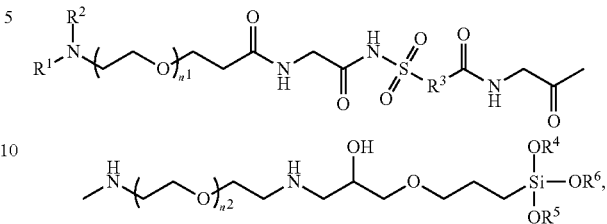

or a salt thereof,
wherein $n^1$=1-15 and $n^2$=1-6; and
wherein $R^1$ and $R^2$ are the same or different and are independently hydrogen or acyloxy;
$R^3$ is alkyl, alkenyl, alkynyl or aryl, all optionally substituted with 1, 2, 3, or 4 groups selected from hydrogen, halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl; and
$R^4$, $R^5$, and $R^6$ are the same or different and are independently selected from hydrogen, alkyl, silyl, or siloxy.

2. The molecule or salt of claim 1, wherein $R^3$ is p-phenyl or n-propyl.

3. The molecule or salt of claim 1, wherein $R^1$ or $R^2$ further comprises a peptide.

4. The molecule or salt of claim 3, wherein said peptide comprises from 2 to 100 amino acids.

5. An array comprising the molecule or salt of claim 1.

6. The array of claim 5, wherein said array comprises at least about 10,000, 300,000, or 1 million peptide features per 1 cm$^2$.

7. The array of claim 5, further comprising a binding moiety.

8. The array of claim 7, wherein said binding moiety comprises a nucleoside, nucleotide, polynucleotide, peptide, peptoid, saccharide, polysaccharide, aptamer, or antibody or fragment thereof.

9. The array of claim 5, further comprising a fatty acid.

10. The array of claim 9, wherein said fatty acid is a fluorinated fatty acid.

11. The molecule or salt of claim 3, wherein said peptide comprises an α-peptide, a β-peptide, or a γ-peptide.

12. The molecule or salt of claim 1, wherein $R^4$, $R^5$, or $R^6$ is linked to a solid phase.

13. The molecule or salt of claim 12, wherein said solid phase comprises a substrate, a bead, or a chromatographic packing material.

14. The molecule or salt of claim 13, wherein said substrate is a Si/SiO$_2$ wafer.

15. The molecule or salt of claim 13, wherein said substrate is a slide or plate configuration.

16. The molecule or salt of claim 15, wherein said plate configuration is a rectangular or disc configuration.

17. The molecule or salt of claim 13, wherein said substrate is organic or inorganic.

18. The molecule or salt of claim 13, wherein said substrate is metal or non-metal.

19. The molecule or salt of claim 18, wherein said metal comprises copper or silver.

20. The molecule or salt of claim 13, wherein said substrate is a polymer or nonpolymer.

21. The molecule or salt of claim 13, wherein said substrate is conducting, semiconducting, or nonconducting.

22. The molecule or salt of claim 13, wherein said substrate is reflecting or nonreflecting.

23. The molecule or salt of claim 13, wherein said substrate is porous or nonporous.

* * * * *